United States Patent [19]

Kaneko et al.

[11] Patent Number: 5,391,564
[45] Date of Patent: * Feb. 21, 1995

[54] RHIZOXIN DERIVATIVES AND THEIR USE AS ANTI-TUMOR AGENTS

[75] Inventors: Masakatsu Kaneko; Makoto Kamokari; Tomowo Kobayashi; Kazuhiko Sasagawa, all of Hiromachi, Japan

[73] Assignee: Sankyo Company, Limited, Tokyo, Japan

[*] Notice: The portion of the term of this patent subsequent to Oct. 4, 2011 has been disclaimed.

[21] Appl. No.: 195,574

[22] Filed: Feb. 14, 1994

Related U.S. Application Data

[63] Continuation of Ser. No. 928,889, Aug. 12, 1992, abandoned, which is a continuation of Ser. No. 737,252, Jul. 26, 1991, abandoned, which is a continuation of Ser. No. 520,979, May 8, 1990, abandoned, which is a continuation of Ser. No. 375,869, Jul. 5, 1989, abandoned.

[30] Foreign Application Priority Data

Jul. 6, 1988 [JP] Japan .................. 63-168152

[51] Int. Cl.⁶ .......................................... C07D 493/18
[52] U.S. Cl. ............................. 514/374; 548/235; 548/236
[58] Field of Search .................. 548/235, 236; 514/374

[56] References Cited

FOREIGN PATENT DOCUMENTS

| | | | |
|---|---|---|---|
| 350315 | 1/1990 | European Pat. Off. | 548/236 |
| 62-87 | 1/1987 | Japan . | |
| 196789 | 8/1990 | Japan | 548/236 |

OTHER PUBLICATIONS

Burger, "Medicinal Chemistry 2d Ed.", Interscience, N.Y., 1960, p. 42.
Ueda et al., Chem. Abstr., vol. 113, entry 218230y abstracting Japan 02196789 (1990).

Kaneko et al., Chem. Abstr., vol. 113, entry 114948x abstracting Europe 350 315 (1990).

*Primary Examiner*—Donald G. Daus
*Attorney, Agent, or Firm*—Frishauf, Holtz, Goodman & Woodward

[57] ABSTRACT

Rhizoxin and rhizoxin-2-ene derivatives of formula (I):

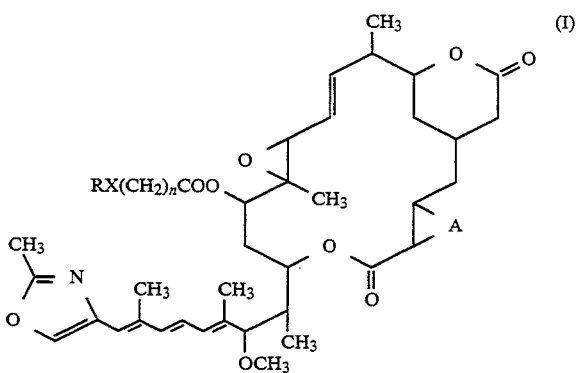

in which: n is 1 to 25: A is an extra bond or oxygen, X is oxygen, sulfur, nitrogen or carbonyl; and R is hydrogen, carboxylic acyl having from 1 to 25 carbon atoms, alkoxycarbonyl group having from 2 to 26 carbon atoms, phosphono, alkylphosphono group in which the alkyl part has from 1 to 25 carbon atoms, dialkylphosphono group in which each alkyl part has from 1 to 25 carbon atoms, alkyl group having from 1 to 25 carbon atoms, aralkyl, cycloalkyl, heterocyclic, alkylthio group in which the alkyl part has from 1 to 25 carbon atoms, aralkylthio, or heterocyclylthio, or when X represents a nitrogen atom, R is $R^1$ and $R^2$, where $R^1$ and $R^2$ are hydrogen, alkyl, acyl, alkoxycarbonyl, phosphono, alkylphosphono or dialkylphosphono have valuable anti-tumor activity. They may be prepared by acylation of rhizoxin or rhizoxin-2-ene.

6 Claims, No Drawings

RHIZOXIN DERIVATIVES AND THEIR USE AS ANTI-TUMOR AGENTS

This application is a continuation of application Ser. No. 07/928,889, filed Aug. 12, 1992, (abandoned), which is a continuation of application Ser. No. 07/737,252, Filed Jul. 26, 1991, (abandoned), which is a continuation of application Ser. No. 07/520,979, filed May 8, 1990,(abandoned), which is a continuation of application Ser. 10 No. 07/375,869, filed Jul. 5, 1989, (abandoned).

BACKGROUND TO THE INVENTION

The present invention relates to a series of new derivatives of the known compounds, rhizoxin and its corresponding ting-opened acid. The invention also provides methods and compositions using these compounds as well as processes for their preparation.

Rhizoxin itself is a known compound having the following formula (A):

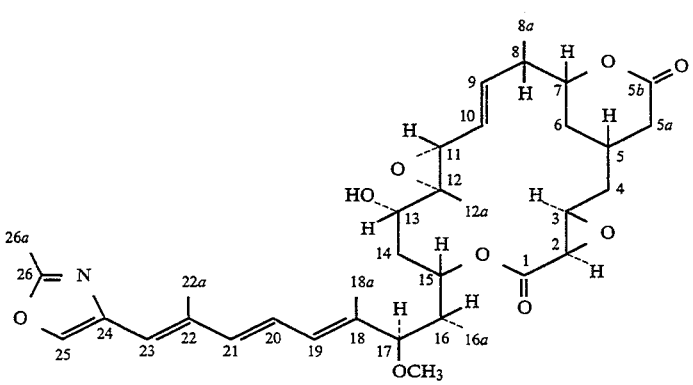

[J. Antibiotics, 37, 354–362 (1984)], and it and its acetate are also known to have an anti-tumor effect [Cancer Res., 46, 381–385 (1986)]. It has also been reported that the mechanism by which it operates is the inhibition of cell division caused by inhibiting the growth of microtubules [J. Antibiotics, 40, 66–63 (1987)]. In accordance with the recommendations of the International Union of Pure and Applied Chemistry, "Nomenclature of Organic Chemistry" Section F, the compounds of the present invention are named as derivatives of rhizoxin and its corresponding ring-opened acid, taking rhizoxin as the base compound and using the numbering system shown on the above formula (A).

Rhizoxin-2-ene was reported on 18th Dec. 1984 to the 1984 International Chemical Congress of the Pacific Basin Society, Honolulu, Hi.

Subsequently, certain specific derivatives of rhizoxin, of rhizoxin-2-ene and of their corresponding ring-opened acids in which the 13-hydroxy group had been acylated by an alkanoyl group having at least 3 carbon atoms were disclosed in U.S. Pat. No. 4,791,128, and were found to have far better anti-tumor activity than rhizoxin and its acetate and a lower toxicity than rhizoxin itself.

We have now discovered an unusual series of rhizoxin derivatives, which, like the compounds of U.S. Pat. No. 4,791,128 are acylated at the 13-position, but which have substantially better activity and lower toxicity.

BRIEF SUMMARY OF THE INVENTION

It is an object of the present invention to provide a series of new compounds having an improved anti-tumor activity, especially against non-solid tumors.

In accordance with the present invention, there are provided compounds of formula (I):

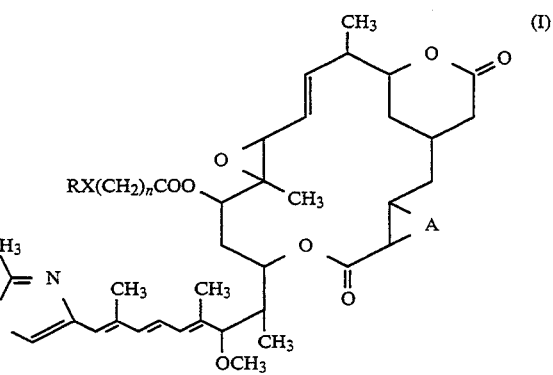

in which:
n represents an integer of from 1 to 25,
A represents an extra carbon-carbon bond or an oxygen atom,
X represents an oxygen, sulfur or nitrogen atom or a carbonyl ($>C=O$) group and
when X represents an oxygen atom,
R represents: a hydrogen atom; an aliphatic carboxylic acyl group having from 1 to 25 carbon atoms, which group is unsubstituted or has at least one substituent selected from the group consisting of substituents (a), defined below; an alkoxycarbonyl group in which the alkoxy part has from 1 to 25 carbon atoms and is unsubstituted or has at least one substituent selected from the group consisting of substituents (a), defined below; a phosphono group; an alkylphosphono group in which the alkyl part has from 1 to 25 carbon atoms and is unsubstituted or has at least one substituent selected from the group consisting of substituents (a), defined below; or a dialkylphosphono group in which each alkyl part has from 1 to 25 carbon atoms and is unsubstituted or has at least one substituent selected from the group consisting of substituents (a), defined below;
when X represents a sulfur atom,
R represents: a hydrogen atom: an alkyl group which has from 1 to 25 carbon atoms and is unsubstituted or has at least one substituent selected from the group consisting of substituents (b), defined below: an aralkyl group in which the alkyl part has from 1 to 25 carbon atoms and the aryl part is a carbocyclic aryl group which has from 6 to 18 ring carbon atoms and is unsubstituted or has at least one substituent selected from the group consisting of substituents (c), defined below: a $C_3-C_7$ cycloalkyl group which is unsubstituted or has at least one substituent selected from the group consisting of substituents (c), defined below; a monocyclic heterocyclic group having from 5 to 7 ring atoms of which from 1 to 3 are hetero-atoms selected from the group consisting of nitrogen, oxygen and sulfur atoms, said group being unsubstituted or having at least one substituent selected from the group consisting of substituents (c), defined below; a fused polycyclic heterocyclic group in which the heterocyclic part has from 5 to 7 ring atoms of which from 1 to 3 are hereto-atoms selected from the group consisting of nitrogen, oxygen and sulfur atoms and is fused to a benzene ring, said group being unsubstituted or having at least one substituent selected from the group consisting of substituents (c), defined below; an aliphatic carboxylic acyl group having from 1 to 25 carbon atoms, which group is unsubstituted or has at least one substituent selected from the group consisting of substituents (a), defined below: an alkoxycarbonyl group in which the alkoxy part has from 1 to 25 carbon atoms and is unsubstituted or has at least one substituent selected from the group consisting of substituents (a), defined below: an alkylthio group in which the alkyl part has from 1 to 25 carbon atoms and is unsubstituted or has at least one substituent selected from the group consisting of substituents (a), defined below; an aralkylthio group in which the alkyl part has from 1 to 25 carbon atoms and the aryl part is a $C_6-C_{10}$ carbocyclic aryl group which is unsubstituted or has at least one substituent selected from the group consisting of substituents (c), defined below: a monocyclic heterocyclylthio group having from 5 to 7 ring atoms of which from 1 to 3 are hetero-atoms selected from the group consisting of nitrogen, oxygen and sulfur atoms said group being unsubstituted or having at least one substituent selected from the group consisting of substituents (c), defined below: or a fused polycyclic heterocyclylthio group in which the heterocyclic part has from 5 to 7 ring atoms of which from 1 to 3 are hetero-atoms selected from the group consisting of nitrogen, oxygen and sulfur atoms and is fused to a benzene ring, said group being unsubstituted or having at least one substituent selected from the group consisting of substituents (c), defined below;

when X represents a nitrogen atom,

R represents $R^1$ and $R^2$ i.e. R—X— represents a group of formula:

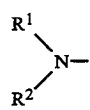

where $R^1$ and $R^2$ are independently selected from the group consisting of hydrogen atoms, alkyl groups, aliphatic carboxylic acyl groups, alkoxycarbonyl groups, phosphono groups, alkylphosphono groups and dialkylphosphono groups, in which said acyl and alkyl groups and the alkyl parts of said alkoxycarbonyl, alkylphosphono and dialkylphosphono groups have from 1 to 25 carbon atoms and are unsubstituted or have at least one substituent selected from the group consisting of substituents (a), defined below:

when X represents a carbonyl group,

R represents a $C_1-C_{25}$ alkoxy group:
substituents (a):
halogen atoms, carboxy groups, hydroxy groups, groups of formula —COO—Rhz, where Rhz is as defined below, 2,4-dicyclohexylallophanyl groups and $C_6-C_{10}$ carbocyclic aryl groups which are unsubstituted or have at least one substituent selected from the group consisting of nitro and cyano groups:
substituents (b):
halogen atoms: carboxy groups: hydroxy groups: groups of formula —COO—Rhz, where Rhz is as defined below: 2,4-dicyclohexylallophanyl groups: $C_6-C_{10}$ carbocyclic aryl groups which are unsubstituted or have at least one substituent selected from the group consisting of nitro and cyano groups: amino groups: $C_1-C_5$ alkylamino groups: dialkylamino groups in which each alkyl part is $C_1-C_5$; $C_2-C_6$ aliphatic acylamino groups; diacylamino groups in which each acyl part is a $C_2-C_6$ carboxylic acyl group; $C_1-C_5$ alkoxy groups; phosphonooxy groups; $C_1-C_5$ alkylphosphonooxy groups: dialkylphosphonooxy groups in which each alkyl part is $C_1-C_5$; mercapto groups; $C_1-C_5$ alkylthio groups; $C_2-C_6$ carboxylic acylthio groups: $C_2-C_6$ alkoxycarbonylthio groups: $C_2-C_6$ alkylthiocarbonyl groups; carbamoyl groups: N-alkylcarbamoyl groups in which the alkyl part is $C_1-C_5$; and N,N-dialkylcarbamoyl groups in which each alkyl part is $C_1-C_5$;
substituents (c):
$C_1-C_5$ alkyl groups; $C_1-C_5$ alkoxy groups: hydroxy groups: mercapto groups: cyano groups: nitro groups; $C_1-C_5$ haloalkyl groups; $C_1-C_3$ alkylenedioxy groups; halogen atoms; $C_2-C_6$ carboxylic acyloxy groups: amino groups; $C_1-C_5$ alkylamino groups: $C_2-C_6$ carboxylic acylamino groups; $C_1-C_5$ alkylthio groups: $C_2-C_6$ carboxylic acylthio groups: carboxy groups: carbamoyl groups; N-alkylcarbamoyl groups in which the alkyl part is $C_1-C_5$; N,N-dialkylcarbamoyl groups in which each alkyl part is $C_1-C_5$; and $C_2-C_6$ alkylthiocarbonyl groups;

Rhz represents a group of formula (II):

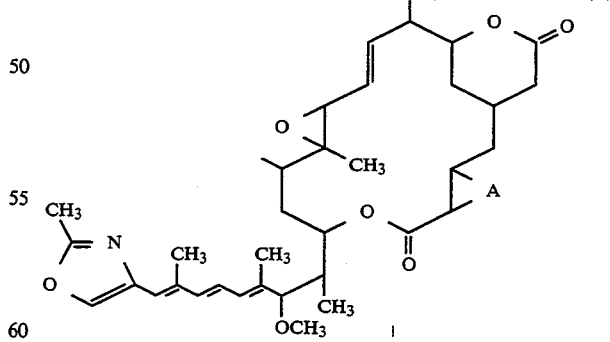

and the ring-opened acid corresponding to said compound of formula (I) and salts and esters of said acid.

The invention also provides a pharmaceutical composition comprising an anti-tumor agent in admixture with a pharmaceutically acceptable carrier or diluent, wherein the anti-tumor agent is at least one compound selected from the group consisting of compounds of formula (I), ring-opened acids corresponding to said compounds of formula (I) and pharmaceutically acceptable salts and esters of said ring-opened acids.

The invention still further provides a method of treating an animal, especially mammal, including human being, suffering from tumors, by administering thereto an effective amount of an anti-tumor agent, wherein said anti-tumor agent is at least one compound selected from the group consisting of compounds of formula (I), ring-opened acids corresponding to said compounds of formula (I) and pharmaceutically acceptable salts and esters of said ring-opened acids.

The invention also provides methods of preparing the compounds of the invention, as described in more detail hereafter.

DETAILED DESCRIPTION OF INVENTION

It will be seen that the compounds of formula (I) are lactones and there therefore exist hydroxy-acids corresponding thereto. For the avoidance of doubt, the formula of such acids is as shown in formula (III):

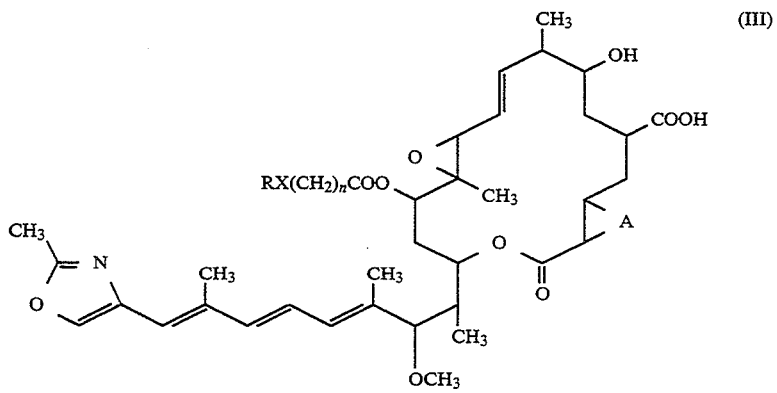

(in which n, A and R are as defined above). In the compounds of formula (III), where the group represented by R includes a group of formula Rhz (II), this group of formula (II) may likewise be in the form of its ring-opened equivalent.

In the compounds of the present invention, where A represents an oxygen atom, the compound is a derivative of rhizoxin itself. Where A represents an extra carbon-carbon bond, the compounds are derivatives of rhizoxin-2-ene. The nomenclature of such compounds is explained hereafter.

In the compounds of the present invention, where X represents an oxygen or sulfur atom and R represents an aliphatic carboxylic acyl group or where X represents a nitrogen atom and $R^1$ or $R^2$ represents an aliphatic carboxylic acyl group, the acyl group may have from 1 to 25 carbon atoms and may have a saturated or unsaturated carbon chain. In the case of a saturated carbon chain, the group is a $C_1$-$C_{25}$ alkanoyl group, preferably a $C_2$-$C_{25}$ alkanoyl group: in the case of an unsaturated carbon chain, the group is a $C_3$-$C_{25}$ alkenoyl or alkynoyl group, preferably an alkenoyl group, which may have one or more carbon-carbon double or triple bonds. Examples of such aliphatic carboxylic acyl groups include the acetyl, propionyl, butyryl, isobutyryl, 2-methylpropionyl, pentanoyl, 2-methylbutyryl, pivaloyl, valeryl, isovaleryl, hexanoyl, 2-methylpentanoyl, 3-methylpentanoyl, 4-methylpentanoyl, heptanoyl, 2-methylhexanoyl, 3-ethylhexanoyl, octanoyl, 2-methylheptanoyl, 3-ethylheptanoyl, 2-ethyl-3-methylpentanoyl, 3-ethyl-2-methylpentanoyl, nonanoyl, 2-methyloctanoyl, 7-methyloctanoyl, 4-ethylheptanoyl, 3-ethyl-2-methylhexanoyl, 2-ethyl-1-methylhexanoyl, decanoyl, 2-methylnonanoyl, 8-methylnonanoyl, 5-ethyloctanoyl, 3-ethyl-2-methylheptanoyl, 3,3-diethylhexanoyl, undecanoyl, 2-methyldecanoyl, 9-methyldecanoyl, undecenoyl, 2-methyldecenoyl, 9-methyldecenoyl, 4-ethylnonanoyl, 3,5-dimethylnonanoyl, 3-propyloctanoyl, 5-ethyl-4-methyloctanoyl, dodecanoyl, 1-methylundecanoyl, 10-methylundecanoyl, 3-ethyldecenoyl, 5-propylnonyl, 3,5-diethyloctanoyl, tridecanoyl, 11-methyldodecanoyl, 7-ethylundecenoyl, 4-propyldecenoyl, 5-ethyl-3-methyldecenoyl-3-pentyloctahoyl, tetradecanoyl, 12-methyltridecanoyl, 8-ethyldodecanoyl, 6-propylundecanoyl, 4-butyldecenoyl, 2-pentylnonanoyl, pentadecanoyl, 13-methyltetradecenoyl, 10-ethyltridecenoyl, 7-propyldodecanoyl, 5-ethyl-3-methyldodecanoyl, 4-pentyldecanoyl, hexadecanoyl, 14-methylpentadec anoyl, 6-ethyltetradecanoyl, 4-propyltridecanoyl, 2-butyldodecanoyl, heptadecanoyl, 15-methylhexadecanoyl, 7-ethylpentadecanoyl, 3-propyltetradecanoyl, 5- pentyldodedodecanoyl, octadecanoyl, 16-methylheptadecanoyl, 5-propylpentadecanoyl, nonadecanoyl, 17-methyloctadecanoyl, 4-ethylheptadecanoyl, icosanoyl, 18-methylnonadecanoyl, 3-ethyloctadecanoyl, henicosanoyl, docosanoyl, tricosanoyl, tetracosanoyl and pentacosanoyl. Such groups may be unsubstituted or they may have one or more of substituents (a), defined above and exemplified below.

Where X represents an oxygen or sulfur atom and R represents an alkoxycarbonyl group, an alkylphosphono group, a dialkylphosphono group or an alkylthio group or X represents a nitrogen atom and $R^1$ or $R^2$ represents an alkyl group, an alkoxycarbonyl group, an alkylphosphono group or a dialkylphosphono group, the alkyl part or parts of each such group has or have from 1 to 25 carbon atoms, and examples of such groups include the methyl, ethyl, propyl, 1-methylethyl, butyl, 1-methylpropyl, 2-methylpropyl, 1,1-dimethylethyl, pentyl, 3-methylbutyl, 2,2-dimethylpropyl, 1,1-dimethylpropyl, hexyl, 1-methylpentyl, 2-methylpentyl, 3-methylpentyl, 4-methylpentyl, heptyl, 1-methylhexyl, 2-methylhexyl, 5-methylhexyl, 3-ethylpentyl, octyl, 2-methylheptyl, 5-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, dodecyl, 1- methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6-propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl, 3-ethyloctadecyl, henicosyl, docosyl, tricosyl, tetracosyl and pentacosyl groups.

These alkyl groups may be unsubstituted or they may have one or more substituents selected from the group consisting of substituents (a), defined above. Examples of such substituents include:

halogen atoms, such as the fluorine, chlorine, bromine and iodine atoms:

the carboxy group;

the hydroxy group; and the group of formula —COORhz, where Rhz is a group of formula (II), defined above;

the 2,4-dicyclohexylallophanyl group, which has the formula —CON(cHx)CONH(cHx) (wherein cHx represents a cyclohexyl group):

aryl groups having from 6 to 10, preferably 6 or 10, ring carbon atoms, for example the phenyl or naphthyl (1- or 2- naphthyl) groups, which may be unsubstituted or may themselves be substituted by at least one and preferably from 1 to 3, more preferably 1, substituent selected from the group consisting of nitro and cyano groups, for example the phenyl, o-, m- or R- nitrophenyl and o-, m- or p-cyanophenyl groups.

Where X represents a sulfur atom and R represents an alkyl group, this has from 1 to 25 carbon atoms, and examples of such groups include the alkyl groups exemplified above; such alkyl groups may be unsubstituted or may have at least one substituent selected from the group consisting of substituents (b), defined above and exemplified below.

Examples of such substituents (b) include:

halogen atoms, such as the fluorine, chlorine, bromine and iodine atoms:

the carboxy group;

the hydroxy group; and the group of formula —COORhz, where Rhz is a group of formula (II), defined above;

the 2,4-dicyclohexylallophanyl group, which has the formula —CON(cHx)CONH(cHx) (wherein cHx represents a cyclohexyl group);

aryl groups having from 6 to 10, preferably 6 or 10, ring carbon atoms, for example the phenyl or naphthyl (1- or 2- naphthyl) groups, which may be unsubtituted or may themselves be substituted by at least one, and preferably from 1 to 3, more preferably 1, substituent selected from the group consisting of nitro and cyano groups, for example the phenyl, o-, m- or R- nitrophenyl and o-, m- or p-cyanophenyl groups:

the amino group:

N-alkylamino and N,N-dialkylamino groups, in which the or each alkyl part has from 1 to 5 carbon atoms, for example the methylamino, ethylamino, propylamino, isopropylamino, butylamino, sec-butylamino. t-butylamino, pentylamino, isopentylamino, neopentylamino, t-pentylamino, 1,2-dimethylpropylamino, 1-ethylpropylamino, dimethylamino, diethylamino, dipropylamino, dibutylamino, diisobutylamino, dipentylamino, N-methyl-N-ethylamino, N-methyl-N-propylamino, N-methyl-M-butylamino, N-ethyl-N-propylamino and N-ethyl-N-butylamino groups;

N-acylamino and N,N-diacylamino groups, in which each acyl part has from 2 to 6 carbon atoms and is an aliphatic carboxylic acyl group, e.g. an alkanoyl, alkenoyl or alkynoyl group; examples of the acylamino and diacylamino groups include the acetamido, propionamido, butyrylamino, isobutyrylamino, valeramido, isovaleramido, pivaloylamino, hexanoylamino, N,N-diacetylamino and N,N-dipropionylamino groups;

$C_1$–$C_5$, preferably $C_1$–$C_4$, alkoxy groups, such as the methoxy, ethoxy, propoxy, isopropoxy, butoxy, sec-butoxy, t-butoxy, pentyloxy, isopentyloxy, neopentyloxy and t-pentyloxy groups;

the phosphonooxy, alkylphosphonooxy and dialkylphosphonooxy groups, in each of which the alkyl group is $C_1$–$C_5$, for example the phosphonooxy, methylphosphonooxy, dimethylphosphonooxy, ethylphosphonooxy, diethylphosphonooxy, propylphosphonooxy, dipropylphosphonooxy, isopropylphosphonooxy, diisopropylphosphonooxy, butyl-phosphonooxy, dibutylphosphonooxy, isobutylphosphonooxy, diisobutylphosphonooxy, sec-butylphosphonooxy, di-sec-butylphosphonooxy, t-butylphosphonooxy, di-t-butylphosphonooxy, pentylphosphonooxy, dipentylphosphonooxy, isopentylphosphonooxy, diisopentylphosphonooxy, neopentylphosphonooxy, dineopentylphosphonooxy, t-pentylphosphonooxy, and di-t-pentylphosphonooxy groups;

the mercapto and alkylthio groups, in which the alkyl group is $C_1$–$C_5$, for example the mercapto. methylthio, ethylthio, propylthio, isopropylthio, butylthio, isobutylthio, sec-butylthio, t-butylthio, pentylthio, isopentylthio, neopentylthio and t-pentylthio groups;

N-acylthio groups, in which the acyl part has from 2 to 6 carbon atoms and is an aliphatic carboxylic acyl group, e.g. an alkanoyl, alkenoyl or alkynoyl group; examples groups include the acetylthio, propionylthio, butyrylthio, isobutyrylthio, valerylthio, isovalerylthio, pivaloylthio and hexanoylthio groups;

$C_2$–$C_6$, preferably $C_2$–$C_5$, alkoxycarbonyl groups (i.e. the alkoxy part has from 1 to 5, preferably from 1 to 4, carbon atoms), such as the methoxycarbonyl, ethoxycarbonyl, propoxycarbonyl, isopropoxycarbonyl, butoxycarbonyl, sec-butoxycarbonyl, t-butoxycarbonyl, pentyloxycarbonyl, isopentyloxycarbonyl, neopentyloxycarbonyl and t-pentyloxycarbonyl groups;

$C_2$–$C_6$, preferably $C_2$–$C_5$, alkylthiocarbonyl groups (i.e. the alkyl part has from 1 to 5, preferably from 1 to 4, carbon atoms), such as the methylthiocarbonyl, ethylthiocarbonyl, propylthiocarbonyl, isopropylthiocarbonyl, butylthiocarbonyl, sec-butylthiocarbonyl, t-butylthiocarbonyl, pentylthiocarbonyl, isopentylthiocarbonyl, neopentylthiocarbonyl and t-pentylthiocarbonyl groups;

the carbamoyl group; and

N-alkylcarbamoyl and N,N-dialkylcarbamoyl groups, in which the or each alkyl part has from 1 to 5 carbon atoms, for example the methylcarbamoyl, ethylcarbamoyl, propylcarbamoyl, isopropylcarbamoyl, butylcarbamoyl, sec-butylcarbamoyl, t-butylcarbamoyl, pentylcarbamoyl, isopentylcarbamoyl, neopentylcarbamoyl, t-pentylcarbamoyl, 1,2-dimethylpropylcarbamoyl, 1-ethylpropylcarbamoyl, dimethylcarbamoyl, diethylcarbamoyl, dipropylcarbamoyl, dibutylcarbamoyl, diisobutylcarbamoyl, dipentylcarbamoyl, N-methyl-N-ethylcarbamoyl, N-methyl-N-propylcarbamoyl, N-methyl-N-butylcarbamoyl, N-ethyl-N-propylcarbamoyl and N-ethyl-N-butylcarbamoyl groups.

Where X represents a carbonyl group, R represents an alkoxycarbonyl group, and the alkyl part of this may be any one of the $C_1$–$C_{25}$ alkyl groups exemplified above, but is unsubstituted.

Where X represents a sulfur atom and R represents an aralkyl or aralkylthio group, the alkyl portion of this contains from 1 to 25, preferably from 1 to 4, carbon atoms and the aryl portion is as generally defined above and may be substituted or unsubstituted and, if substituted has at least one substituent selected from the group consisting of substituents (c), defined above and exemlpified below. The alkyl group may have one or more than one aryl substituent, the maximum number of aryl substituents being restricted only by the number of substitutable positions on the alkyl group, and possibly by steric considerations. In general, we prefer that there should be from 1 to 3 such aryl substituents. Examples of the alkyl groups are as given in relation to the alkyl groups which may be represented by R when X represents a sulfur atom. Examples of such unsubstituted aralkyl groups include the benzyl, phenethyl, 1-phenylethyl (=α-methylbenzyl), 2-phenyl-1-methylethyl, 1-phenyl-1-methylethyl, phenylpropyl (1-, 2- and 3-), 1-naphthylmethyl, 2-naphthylmethyl, diphenylmethyl and triphenylmethyl groups. Examples of the aralkylthio groups are the benzylthio, phenethylthio, 1-phenylethylthio (=α-methylbenzylthio), 2-phenyl-1-methylethylthio, 1-phenyl-1-methylethylthio, phenylpropylthio (1-, 2- and 3-), 1-naphthylmethylthio, 2-naphthylmethylthio, diphenylmethylthio and triphenylmethylthio groups. These aralkyl groups may be unsubstituted or the aryl (e.g. phenyl) part thereof may have at least one substituent selected from the group consisting of substituents (c), defined above, e.g.:

$C_1$–$C_5$, preferably $C_1$–$C_4$, alkyl groups, such as the methyl, ethyl, propyl, isopropyl, butyl, sec-butyl, t-butyl, pentyl, isopentyl, neopentyl and t-pentyl groups:

$C_1$–$C_5$, preferably $C_1$–$C_4$, alkoxy groups, such as the methoxy, ethoxy, propoxy, isopropoxy, butoxy, sec-butoxy, t-butoxy, pentyloxy, isopentyloxy, neopentyloxy and t-pentyloxy groups;

hydroxy, mercapto, carboxy, cyano and nitro groups;

$C_1$–$C_5$, preferably $C_1$–$C_4$, haloalkyl groups, such as the trifluoromethyl, 2,2,2-trichloroethyl, 2-haloethyl (e.g. 2-chloroethyl, 2-fluoroethyl, 2-bromoethyl or 2-iodoethyl), 2,2-dibromoethyl, 2,2,2-tribromoethyl, 5-chloropentyl, 5-bromopentyl and 5-fluotopentyl groups:

$C_1$–$C_3$ alkylenedioxy groups, each of which is preferably attached to 2 adjacent positions of the group which it substitutes, for example the methylenedioxy, dimethylenedioxy and trimethylenedioxy groups, of which the methylenedioxy group is preferred;

halogen atoms, such as the fluorine, chlorine, iodine and bromine atoms, of which the fluorine, chlorine and bromine atoms are preferred, the fluorine and chlorine atoms being most preferred;

N-acyloxy groups, in which the acyl part has from 2 to 6 carbon atoms and is an aliphatic carboxylic acyl group, e.g. an alkanoyl, alkenoyl or alkynoyl group; examples groups include the acetoxy, acryloyloxy, methacryloyloxy, propionyloxy, propioloyloxy, butyryloxy, isobutyryloxy, crotonoyloxy, valeryloxy, isovaleryloxy, pivaloyloxy and hexanoyloxy groups;

the amino group:

N-alkylamino and N,N-dialkylamino groups, in which the or each alkyl part has from 1 to 5 carbon atoms, for example the methylamino, ethylamino, propylamino, isopropylamino, butylamino, sec-butylamino, t-butylamino, pentylamino, isopentylamino, neopentylamino, t-pentylamino, 1,2-dimethylpropylamino, 1-ethylpropylamino, dimethylamino, diethylamino, dipropylamino, dibutylamino, diisobutylamino, dipentylamino, N-methyl-N-ethylamino, N-methyl-N-propylamino, N-methyl-N-butylamino, N-ethyl-N-propylamino and N-ethyl-N-butylamino groups;

N-acylamino and N,N-diacylamino groups, in which each acyl part has from 2 to 6 carbon atoms and is an aliphatic carboxylic acyl group, e.g. an alkanoyl, alkenoyl or alkynoyl group; examples of the acylamino and diacylamino groups include the acetamido, propionamido, butyrylamino, isobutyrylamino, valeramido, isovaleramido, pivaloylamino, hexanoylamino, N,N-diacetylamino and N,N-dipropionylamino groups;

the alkylthio groups, in which the alkyl group is $C_1$–$C_5$, for example the methylthio, ethylthio, propylthio, isopropylthio, butylthio, isobutylthio, sec-butylthio, t-butylthio, pentylthio, isopentylthio, neopentylthio and t-pentylthio groups;

N-acylthio groups, in which the acyl part has from 2 to 6 carbon atoms and is an aliphatic carboxylic acyl group, e.g. an alkanoyl, alkenoyl or alkynoyl group; examples groups include the acetylthio, propionylthio, butyrylthio, isobutyrylthio, valerylthio, isovalerylthio, pivaloylthio and hexanoylthio groups;

$C_2$–$C_6$, preferably $C_2$–$C_5$, alkylthiocarbonyl groups (i.e. the alkyl part has from 1 to 5, preferably from 1 to 4, carbon atoms), such as the methylthiocarbonyl, ethylthiocarbonyl, propylthiocarbonyl, isopropylthiocarbonyl, butylthiocarbonyl, sec-butylthiocarbonyl, t-butylthiocarbonyl, pentylthiocarbonyl, isopentylthiocarbonyl, neopentylthiocarbonyl and t-pentylthiocarbonyl groups;

the carbamoyl group; and

N-alkylcarbamoyl and N,N-dialkylcarbamoyl groups, in which the or each alkyl part has from 1 to 5 carbon atoms, for example the methylcarbamoyl, ethylcarbamoyl, propylcarbamoyl, isopropylcarbamoyl, butylcarbamoyl, sec-butylcarbamoyl, t-butylcarbamoyl, pentylcarbamoyl, isopentylcarbamoyl, neopentylcarbamoyl, t-pentylcarbamoyl, 1,2-dimethylpropylcarbamoyl, 1-ethylpropylcarbamoyl, dimethylcarbamoyl, diethylcarbamoyl, dipropylcarbamoyl, dibutylcarbamoyl, diisobutylcarbamoyl, dipentylcarbamoyl, N-methyl-N-ethylcarbamoyl, N-methyl-N-propylcarbamoyl, N-methyl-N-butylcarbamoyl, N-ethyl-N-propylcarbamoyl and N-ethyl-N-butylcarbamoyl groups.

Where R represents an aralkyl or aralkylthio group, it is more preferably an aralkyl or aralkylthio group in which the alkyl part is $C_1$-$C_3$ and the aryl part is a phenyl group, which may be substituted or unsubstituted, where the substituent is at least as defined above, but it is preferably unsubstituted.

Where X represents a sulfur atom and R represents a heterocyclic group or a heterocyclylthio group, the heterocyclic part of this group has from 5 to 7 ring atoms, of which from 1 to 3 are hereto-atoms selected from the group consisting of nitrogen, oxygen and sulfur atoms. The heterocyclic group is optionally fused to a benzene ring to form a bicyclic group. The group is unsubstituted or has at least one substituent selected from the group consisting of substituents (c), defined and exemplified above. Examples of unsubstituted heterocyclic groups include the thienyl, furyl, pyranyl, pyrrolyl, imidazolyl, pyrazolyl, thiazolyl, isothiazolyl, triazolyl, oxazolyl, isoxazolyl, pyridyl, pyrazinyl, pyrimidinyl, pyridazinyl, furazanyl, pyrrolidinyl, pyrrolinyl, imidazolidinyl, imidazolinyl, pyrazolidinyl, pyrazolinyl, piperidyl (e.g. piperidino and 4-piperidyl), piperazinyl, morpholinyl, thiomorpholinyl, azepinyl, benzofuranyl, isobenzofuranyl, chromenyl, indolyl, isoindolyl, quinolyl, isoquinolyl, naphthyridinyl, quinoxalinyl, quinazolinyl, cinnolinyl, chromanyl, isochromanyl, indolinyl and isoindolinyl groups. Examples of such substituted heterocyclic groups include the 6-chloro-3-pyridyl, 6-(trifluoromethyl)-3-pyridyl, 5-chloro-2-pyridyl, 5-(trifluoromethyl)-2-furyl, 5-(trifluoromethyl)-2-thienyl, 5-chloro-2-thienyl and quinolyl (e.g. 2-quinolyl) groups.

Where X represents a sulfur atom and R represents a cycloalkyl group, this has from 3 to 7 ring atoms and may be unsubstituted or may have at least one substituent selected from the group consisting of substituents (c), defined and exemplified above. Examples of the unsubstituted cycloalkyl groups include the cyclopropyl, cyclobutyl, cyclopentyl, cyclohexyl and cycloheptyl groups.

Of the compounds of the present invention, the following are preferred classes:

1. Compounds of formula (I), wherein A represents an oxygen atom and pharmaceutically acceptable salts and esters thereof.
2. Compounds of formula (I), wherein n is an integer from 1 to 20 and pharmaceutically acceptable salts and esters thereof.
3. Compounds of formula (I), wherein X represents an oxygen atom and R represents: a hydrogen atom; an aliphatic carboxylic acyl group having from 2 to 22 carbon atoms, which group is unsubstituted or has at least one substituent selected from the group consisting of substituents ($a^1$), defined below; an alkoxycarbonyl group in which the alkoxy part has from 1 to 20 carbon atoms and is unsubstituted or has at least one substituent selected from the group consisting of substituents ($a^1$), defined below; a phosphono group; an alkylphosphono group in which the alkyl part has from 1 to 10 carbon atoms and is unsubstituted or has at least one substituent selected from the group consisting of substituents ($a^1$), defined below; or a dialkylphosphono group in which each alkyl part has from 1 to 10 carbon atoms and is unsubstituted or has at least one substituent selected from the group consisting of substituents ($a^1$), defined below;

substituents ($a^1$):
halogen atoms, hydroxy groups, groups of formula —COO—Rhz, where Rhz is as defined below, 2,4-dicyclohexylallophanyl groups and phenyl groups which are unsubstituted or have at least one substituent selected from the group consisting of nitro and cyano groups and pharmaceutically acceptable salts and esters thereof.

4. Compounds of formula (I), wherein X represents a sulfur atom and R represents: a hydrogen atom; an alkyl group which has from 1 to 20 carbon atoms and is unsubstituted or has at least one substituent selected from the group consisting of substituents ($b^1$), defined below; an aralkyl group in which the alkyl part has from 1 to 4 carbon atoms and the aryl part is a phenyl group which is unsubstituted or has at least one substituent selected from the group consisting of substituents ($c^1$), defined below; a monocyclic heterocyclic group having from 5 to 7 ring atoms of which 1 or 2 are hereto-atoms selected from the group consisting of nitrogen, oxygen and sulfur atoms, said group being unsubstituted or having at least one substituent selected from the group consisting of substituents ($c^1$), defined below: an aliphatic carboxylic acyl group having from 2 to 24 carbon atoms, which group is unsubstituted or has at least one substituent selected from the group consisting of substituents ($a^1$), defined in (3) above: an alkoxycarbonyl group in which the alkoxy part has from 1 to 20 carbon atoms and is unsubstituted or has at least one substituent selected from the group consisting of substituents ($a^1$), defined in (3) above: an alkylthio group in which the alkyl part has from 1 to 10 carbon atoms and is unsubstituted or has at least one substituent selected from the group consisting of substituents ($a^1$), defined in (3) above: an aralkylthio group in which the alkyl part has from 1 to 4 carbon atoms and the aryl part is a phenyl group which is unsubstituted or has at least one substituent selected from the group consisting of substituents ($c^1$), defined below: or a monocyclic heterocyclylthio group having from 5 to 7 ring atoms of which 1 or 2 are hetero-atoms selected from the group consisting of nitrogen, oxygen and sulfur atoms, said group being unsubstituted or having at least one substituent selected from the group consisting of substituents ($c^1$), defined below;

substituents ($b^1$):
halogen atoms: hydroxy groups: groups of formula —COO—Rhz, where Rhz is as defined below; 2,4-dicyclohexylallophanyl groups: phenyl groups which are unsubstituted or have at least one substituent selected from the group consisting of nitro and cyano groups; amino groups: $C_1$-$C_5$ alkylamino groups; dialkylamino groups in which each alkyl part is $C_1$-$C_5$; $C_2$-$C_6$ aliphatic acylamino groups:

$C_1$-$C_5$ alkoxy groups: mercapto groups: $C_1$-$C_5$ alkylthio groups: $C_2$-$C_6$ carboxylic acylthio groups: $C_2$-$C_6$ alkoxycarbonylthio groups: $C_2$-$C_6$ alkylthiocarbonyl groups: carbamoyl groups: N-alkylcarbamoyl groups in which the alkyl part is $C_1$-$C_5$, and N N-dialkylcarbamoyl groups in which each alkyl part is $C_1$-$C_5$; and substituents ($c^1$):

$C_1$–$C_5$ alkyl groups: $C_1$–$C_5$ alkoxy groups; hydroxy groups; mercapto groups; cyano groups; nitro groups; $C_1$–$C_5$ haloalkyl groups; halogen atoms; $C_2$–$C_6$ carboxylic acyloxy groups; amino groups; $C_1$–$C_5$ alkylamino groups; $C_2$–$C_6$ carboxylic acylamino groups; $C_1$–$C_5$ alkylthio groups; $C_2$–$C_6$ carboxylic acylthio groups; carbamoyl groups; N-alkylcarbamoyl groups in which the alkyl part is $C_1$–$C_5$; N,N-dialkylcarbamoyl groups in which each alkyl part is $C_1$–$C_5$; and $C_2$–$C_6$ alkylthiocarbonyl groups;

and pharmaceutically acceptable salts and esters thereof.

5. Compounds of formula (I), wherein X represents a nitrogen atom and $R^1$ and $R^2$ are independently selected from the group consisting of: hydrogen atoms; $C_1$–$C_{10}$ alkyl groups; $C_2$–$C_{24}$ aliphatic carboxylic acyl groups; alkoxycarbonyl groups in which the alkoxy part has from 2 to 20 carbon atoms; phosphono groups; alkylphosphono groups and dialkylphosphono groups in which the or each alkyl part has from 1 to 12 carbon atoms; in which said acyl and alkyl groups and the alkyl parts of said alkoxycarbonyl, alkylphosphono and dialkylphosphono groups are unsubstituted or have at least one substituent selected from the group consisting of substituents ($a^1$), defined in (3) above;

and pharmaceutically acceptable salts and esters thereof.

6. Compounds of formula (I), wherein X represents a carboxy group and R represents a $C_6$–$C_{20}$ alkoxy group and pharmaceutically acceptable salts and esters thereof.

The following are the more preferred classes of compounds of the present invention:

7. Compounds of formula (I), wherein n is an integer from 2 to 15 and pharmaceutically acceptable salts and esters thereof.

8. Compounds of formula (I), wherein X represents an oxygen atom and R represents; a hydrogen atom; an aliphatic carboxylic acyl group having from 2 to 14 carbon atoms, which group is unsubstituted or has at least one substituent selected from the group consisting of substituents ($a^2$), defined below: an alkoxycarbonyl group in which the alkoxy part has from 2 to 16 carbon atoms and is unsubstituted or has at least one substituent selected from the group consisting of substituents ($a^1$), defined below: a phosphono group; an alkylphosphono group in which the alkyl part has from 1 to 6 carbon atoms: or a dialkylphosphono group in which each alkyl part has from 1 to 6 carbon atoms;

substituents ($a^2$):
halogen atoms, hydroxy groups, groups of formula —COO—Rhz, where Rhz is as defined below, and 2,4-dicyclohexylallophanyl groups;

and pharmaceutically acceptable salts and esters thereof.

9. Compounds of formula (I), wherein X represents a sulfur atom and R represents: a hydrogen atom; an alkyl group which has from 1 to 10 carbon atoms and is unsubstituted or has at least one substituent selected from the group consisting of substituents ($b^2$), defined below; a benzyl group which is unsubstituted or has at least one substituent selected from the group consisting of substituents ($c^2$), defined below; a monocyclic heterocyclic group having from 5 to 6 ring atoms of which 1 is a hereto-atom selected from the group consisting of nitrogen, oxygen and sulfur atoms, said group being unsubstituted or having at least one substituent selected from the group consisting of substituents ($c^2$), defined below; an alkanoyl group having from 2 to 16 carbon atoms: an alkoxycarbonyl group in which the alkoxy part has from 1 to 10 carbon atoms; an alkylthio group in which the alkyl part has from 1 to 6 carbon atoms and is unsubstituted or has at least one substituent selected from the group consisting of substituents ($a^2$), defined in (8) above; a benzylthio group which is unsubstituted or has at least one substituent selected from the group consisting of substituents ($c^2$), defined below; or a monocyclic heterocyclylthio group having from 5 to 6 ring atoms of which 1 is a hereto-atom selected from the group consisting of nitrogen, oxygen and sulfur atoms, said group being unsubstituted or having at least one substituent selected from the group consisting of substituents ($c^2$), defined below;

substituents ($b^2$):
halogen atoms; hydroxy groups; groups of formula —COO—Rhz, where Rhz is as defined below; 2,4-dicyclohexylallophanyl groups; amino groups; $C_1$–$C_3$ alkylamino groups; dialkylamino groups in which each alkyl part is $C_1$–$C_3$; $C_1$–$C_3$ alkoxy groups; mercapto groups; $C_1$–$C_5$ alkylthio groups;
$C_2$–$C_6$ carboxylic acylthio groups: $C_2$–$C_6$ alkoxycarbonyl groups; $C_2$–$C_6$ alkylthiocarbonyl groups; carbamoyl groups: N-alkylcarbamoyl groups in which the alkyl part is $C_1$–$C_3$; and N,N-dialkylcarbamoyl groups in which each alkyl part is $C_1$–$C_3$; and substituents ($c^2$):
$C_1$–$C_5$ alkyl groups: $C_1$–$C_5$ alkoxy groups; hydroxy groups; cyano groups; nitro groups; $C_1$–$C_5$ haloalkyl groups; halogen atoms; amino groups; $C_1$–$C_5$ alkylamino groups; $C_2$–$C_6$ carboxylic acylamino groups: carbamoyl groups; N-alkylcarbamoyl groups in which the alkyl part is $C_1$–$C_5$; N,N-dialkylcarbamoyl groups in which each alkyl part is $C_1$–$C_5$; and $C_2$–$C_6$ alkylthiocarbonyl groups;

and pharmaceutically acceptable salts and esters thereof.

10. Compounds of formula (I), wherein X represents a nitrogen atom and $R^1$ and $R^2$ are independently selected from the group consisting of: hydrogen atoms; $C_1$–$C_6$ alkyl groups; $C_2$–$C_{16}$ aliphatic carboxylic acyl groups; alkoxycarbonyl groups in which the alkoxy part has from 2 to 6 carbon atoms; phosphono groups; and $C_1$–$C_{10}$ alkylphosphono groups; in which said acyl and alkyl groups and the alkyl parts of said alkoxycarbonyl and alkylphosphono are unsubstituted or have at least one substituent selected from the group consisting of substituents ($a^2$), defined in (8) above:

and pharmaceutically acceptable salts and esters thereof.

11. Compounds of formula (I), wherein X represents a carboxy group and R represents a $C_6$–$C_{15}$ alkoxy group and pharmaceutically acceptable salts and esters thereof.

The following are the most preferred classes of compounds of the present invention:

12. Compounds of formula (I), wherein n is an integer from 2 to 11 and pharmaceutically acceptable salts and esters thereof.

13. Compounds of formula (I), wherein X represents an oxygen atom and R represents: a hydrogen atom; an aliphatic carboxylic acyl group having from 2 to 11 carbon atoms; an alkoxycarbonyl group in which the alkoxy part has from 2 to 6 carbon atoms and is unsubstituted or has at least one substituent selected from the group consisting of substituents ($a^3$), defined below; a phosphono group; an alkylphosphono group in which the alkyl part has from 1 to 6 carbon atoms; or a dialkylphosphono group in which each alkyl part has from 1 to 6 carbon atoms.

substituents ($a^3$):

halogen atoms, groups of formula —COO—Rhz, where Rhz is as defined below, and 2,4-dicyclohexylallophanyl groups, especially where A also represents an oxygen atom;

and pharmaceutically acceptable salts and esters thereof.

14. Compounds of formula (I), wherein X represents a sulfur atom and R represents: a hydrogen atom; an alkyl group which has from 1 to 10 carbon atoms and is unsubstituted or has at least one substituent selected from the group consisting of substituents ($b^3$), defined below; a monocyclic heterocyclic group having from 5 to 6 ring atoms of which 1 is a hetero-atom selected from the group consisting of nitrogen, oxygen and sulfur atoms; an alkanoyl group having from 2 to 16 carbon atoms; an alkoxycarbonyl group in which the alkoxy part has from 1 to 10 carbon atoms; or an alkylthio group in which the alkyl part has from 1 to 6 carbon atoms and is unsubstituted or has at least one substituent selected from the group consisting of substituents ($a^3$), defined in (13) above; and substituents ($b^3$):

hydroxy groups; groups of formula —COO—Rhz, where Rhz is as defined below; 2,4-dicyclohexylallophanyl groups; amino groups; $C_1$–$C_3$ alkylamino groups; dialkylamino groups in which each alkyl part is $C_1$–$C_3$; mercapto groups; $C_2$–$C_4$ alkoxycarbonyl groups; $C_2$–$C_4$ alkylthiocarbonyl groups; and carbamoyl groups;

especially where A also represents an oxygen atom;

and pharmaceutically acceptable salts and esters thereof.

15. Compounds of formula (I), wherein X represents a nitrogen atom and $R^1$ and $R^2$ are independently selected from the group consisting of: hydrogen atoms; $C_1$–$C_4$ alkyl groups; $C_2$–$C_{16}$ aliphatic carboxylic acyl groups; alkoxycarbonyl groups in which the alkoxy part has from 2 to 6 carbon atoms and is unsubstituted or has at least one substituent selected from the group consisting of substituents ($a^3$), defined in (13) above; phosphono groups; and $C_1$–$C_{10}$ alkylphosphono groups, in which the alkyl part is unsubstituted or has at least one halogen substituent;

especially where A also represents an oxygen atom;

and pharmaceutically acceptable salts and esters thereof.

16. Compounds of formula (I), X represents a carboxy group and R represents a $C_8$–$C_{14}$ alkoxy group, especially where A also represents an oxygen atom;

and pharmaceutically acceptable salts and esters thereof.

The ring-opened acids corresponding to the compounds of formula (I) are free acids and hence can form salts with bases. Provided that the resulting salt is pharmaceutically acceptable, which, as is well-known in the art, means that the salt does not have reduced (or unacceptably reduced) activity or increased (or unacceptably increased) toxicity as compared with the parent acid, there is no restriction on the nature of the cation forming the salt. Examples of suitable salts include metal salts, salts with amino acids and salts with ammonia and organic amines. Examples of suitable metal salts include salts with: alkali metals, such as sodium or potassium; alkaline, earth metals, such as calcium or magnesium; and salts with other pharmaceutically acceptable metals, such as aluminum, iron, zinc, copper, nickel and cobalt. However, the preferred salts are those with alkali metals, alkaline earth metals and aluminum, and the most preferred salts are the sodium, potassium, calcium and aluminum salts. Examples of amino acids with which the compounds of the present invention may form salts include such basic amino acids as arginine, lysine, histadine, $\alpha$, $\gamma$-diaminobutyric acid and ornithine. Examples of amines with which the compounds of formula (I) may form salts include t-octylamine, dibenzylamine, dicyclohexylamine, morpholine, D-phenylglycine alkyl esters and D-glucosamine.

The compounds of the present invention may likewise form esters, and, where the esters are to be used for therapeutic purposes, they, like the salts, should be pharmaceutically acceptable. Esters are well known in this type of compound, and any conventional type of ester may equally be employed in the present invention. However, preferred esters include:

$C_1$–$C_{20}$ alkyl esters, more preferably $C_1$–$C_6$ alkyl esters; $C_3$–$C_7$ cycloalkyl esters; aralkyl esters in which the alkyl part is $C_1$–$C_3$ and the aromatic group is $C_6$–$C_{14}$ and is unsubstituted or has at least one substituent selected from the group consisting of substituents (b), defined above; $C_2$–$C_6$ alkenyl esters in which the alkenyl group is unsubstituted or has at least one substituent selected from the group consisting of substituents (a) defined above; halogenated $C_1$–$C_6$, preferably $C_1$–$C_4$, alkyl esters; substituted silylalkyl esters in which the alkyl part is $C_1$–$C_6$ and the silyl group has up to 3 substituents selected from the group consisting of $C_1$–$C_6$ alkyl groups and phenyl groups which are unsubstituted or have at least one substituent selected from the group consisting of substituents (b) defined above; phenyl esters in which the phenyl group is unsubstituted or has at least one $C_1$–$C_4$ alkyl or acylamino substituent; phenacyl esters in which the phenacyl group is unsubstituted or has at least one substituent selected from the group consisting of substituents (b) defined above; cyclic or acyclic terpenyl esters; alkoxymethyl esters, in which the alkoxy part is $C_1$–$C_6$, preferably $C_1$–$C_4$, and is unsubstituted or is itself substituted by a single unsubstituted alkoxy group: aliphatic acyloxymethyl esters, in which the acyl group is preferably an alkanoyl group and is more preferably a $C_2$–$C_6$ alkanoyl group; higher aliphatic acyloxyalkyl esters in which the acyl group is preferably an alkanoyl group and is more preferably a $C_2$–$C_6$ alkanoyl group, and the alkyl part is $C_2$–$C_6$, and preferably $C_2$–$C_4$; cycloalkyl-substituted aliphatic acyloxyalkyl esters, in which the acyl group is preferably an alkanoyl group and is more preferably a $C_2$–$C_6$ alkanoyl group, the cycloalkyl substituent is $C_3$–$C_7$, and the alkyl part is a $C_1$–$C_6$ alkyl group, preferably a $C_1$–$C_4$ alkyl group; alkoxycarbonyloxyalkyl esters, especially 1-(alkoxycarbonyloxy)ethyl esters, in which the alkoxy part is $C_1$–$C_{10}$, preferably $C_1$–$C_6$, and more preferably $C_1$–$C_4$, and the alkyl part is $C_1$–$C_6$, preferably $C_1$–$C_4$; cycloalkylcarbonyloxyalkyl or cycloalkyloxycarbonyloxyalkyl esters, in which the cycloalkyl group is $C_3$–$C_{10}$, preferably $C_3$–$C_7$, is mono- or poly- cyclic and is optionally substituted by at least one $C_1$–$C_4$ alkyl group, and the alkyl group is a $C_1$–$C_6$, more preferably $C_1$–$C_4$, alkyl group; cycloalkylalkoxycarbonyloxyalkyl esters in which the alkoxy group has a single cycloalkyl substituent, the cycloalkyl substituent being $C_3$–$C_{10}$, preferably $C_3$–$C_7$, and mono- or polycyclic; terpenylcarbonyloxyalkyl or terpenyloxycarbonyloxyalkyl esters: 5-alkyl- or 5-phenyl- substituted (2-oxo-1,3-dioxolen-4-yl)alkyl esters in which each alkyl group is $C_1$–$C_6$, preferably $C_1$–$C_4$, and in which the phenyl group is unsubstituted or has at least one substituent selected from the group consisting of substituents (b), defined above; phthalidyl esters; indanyl esters; and 2-oxo-4,5,6,7-tetrahydro-1,3-benzodioxolen-4-yl esters.

In naming the compounds of the invention, they are named semi-systematically in accordance with the recommendations of the International Union of Pure and Applied Chemistry, "Nomenclature of Organic Chemistry" Section F, taking rhizoxin as the base name. Thus, compounds of formula (I) in which A represents an oxygen atom are simply esters of rhizoxin with an acid of formula $R(CH_2)_nCOOH$ and these are thus named as rhizoxin-13-yl acylates. The ring-opened analog of rhizoxin is called rhizoxin-5b-oic acid and thus compounds of formula (III) in which A represents an oxygen atom are named as the 13-acyloxy derivatives of this, i.e. 13-acyloxy-13-dehydroxyrhizoxin-5b-oic acids. Compounds of formula (I) where A represents an extra carbon-carbon bond are regarded as derivatives of rhizoxin-2-ene, more formally 2,3-deoxyrhizoxin-2-ene. Hence, compounds of formulae (I) and (III) where A represents such a bond are named as 2,3-deoxyrhizoxin-2-en-13-yl acylates and 13-acyloxy-13-dehydroxy-2,3-deoxyrhizoxin-2-en-5b-oic acids, respectively.

Specific examples of compounds of the present invention are given below.
1. Rhizoxin-13-yl 3-hydroxypropionate.
2. Rhizoxin-13-yl 3-(2,2,2-trichloroethoxycarbonyloxy)propionate.
3. Rhizoxin-13-yl 3-decanoyloxypropionate.
4. Rhizoxin-13-yl 3-dodecanoyloxypropionate.
5. Rhizoxin-13-yl 3-tetradecanoyloxypropionate.
6. Rhizoxin-13-yl 3-icosanoyloxypropionate.
7. Rhizoxin-13-yl 4-hydroxybutyrate.
8. Rhizoxin-13-yl 4-(2,2,2-trichloroethoxycarbonyloxy)butyrate.
9. Rhizoxin-13-yl 4-propionyloxybutyrate.
10. Rhizoxin-13-yl 4-heptanoyloxybutyrate.
11. Rhizoxin-13-yl 4-undecanoyloxybutyrate.
12. Rhizoxin-13-yl 4-tricosanoyloxybutyrate.
13. Rhizoxin-13-yl 6-hydroxyhexanoate.
14. Rhizoxin-13-yl 6-acetoxyhexanoate.
15. Rhizoxin-13-yl 6-propionyloxyhexanoate.
16. Rhizoxin-13-yl 6-heptanoyloxyhexanoate.
17. Rhizoxin-13-yl 6-myristoyloxyhexanoate.
18. Rhizoxin-13-yl 9-hydroxynonanoate.
19. Rhizoxin-13-yl 9-hexanoyloxynonanoate.
20. Rhizoxin-13-yl 9-decanoyloxynonanoate.
21. Rhizoxin-13-yl 9-lauroyloxynonanoate.
22. Rhizoxin-13-yl 11-hydroxyundecanoate.
23. Rhizoxin-13-yl 11-methoxycarbonyloxyundecanoate.
24. Rhizoxin-13-yl 11-ethoxycarbonyloxyundecanoate.
25. Rhizoxin-13-yl 11-t-butoxycarbonyloxyundecanoate.
26. Rhizoxin-13-yl 11-heptanoyloxyundecanoate.
27. Rhizoxin-13-yl 12-hydroxydodecanoate.
28. Rhizoxin-13-yl 12-(2,2,2-trichloroethoxycarbonyloxy)dodecanoate.
29. Rhizoxin-13-yl 12-ethoxycarbonyloxydodecanoate.
30. Rhizoxin-13-yl 12-heptyloxycarbonyloxydodecanoate.
31. Rhizoxin-13-yl 12-propionyloxydodecanoate.
32. Rhizoxin-13-yl 12-valeryloxydodecanoate.
33. Rhizoxin-13-yl 12-myristoyloxydodecanoate.
34. Rhizoxin-13-yl 14-(2,2,2-trichloroethoxycarbonyloxy)tetradecanoate.
35. Rhizoxin-13-yl 14-pentyloxycarbonyloxytetradecanoate.
36. Rhizoxin-13-yl 14-hexadecyloxycarbonyloxytetradecanoate.
37. Rhizoxin-13-yl 14-pentadecanoyloxytetradecanoate.
38. Rhizoxin-13-yl 16-hydroxyhexadecanoate.
39. Rhizoxin-13-yl 16-(2,2,2-trichloroethoxycarbonyloxy)hexadecanoate.
40. Rhizoxin-13-yl 16-acetoxyhexadecanoate.
41. Rhizoxin-13-yl 16-phosphonooxyhexadecanoate.
42. Rhizoxin-13-yl 16-(ethoxyphosphonooxy)hexadecanoate.
43. Rhizoxin-13-yl 16-(hexyloxyphosphonooxy)hexadecanoate.
44. Rhizoxin-13-yl 16-(undecyloxyphosphonooxy)hexadecanoate.
45. Rhizoxin-13-yl 16-(dimethoxyphosphonooxy)hexadecanoate.
46. Rhizoxin-13-yl 19-heptanoyloxynonadecanoate.
47. Rhizoxin-13-yl 3-mercaptopropionate.
48. Rhizoxin-13-yl 3-(ethyldithio)propionate.
49. Rhizoxin-13-yl 3-(benzyldithio)propionate.
50. Rhizoxin-13-yl 3,3'-dithiodipropionate.
51. Rhizoxin-13-yl 3-[2-(2,4-dicyclohexylallophanyl)ethyldithio]propionate.
52. Rhizoxin-13-yl 3-(2,2,2-trichloroethoxycarbonylthio)propionate.
53. Rhizoxin-13-yl 3-(acetylthio)propionate.
54. Rhizoxin-13-yl 3-(isovalerylthio)propionate.
55. Rhizoxin-13-yl 3-(heptanoylthio)propionate.
56. Rhizoxin-13-yl 3-(decanoylthio)propionate.
57. Rhizoxin-13-yl 3-(lauroylthio)propionate.
58. Rhizoxin-13-yl 3-(myristoylthio)propionate.
59. Rhizoxin-13-yl 3-(palmitoylthio)propionate.
60. Rhizoxin-13-yl 3-(ethoxyphosphonooxy)propionate.
61. Rhizoxin-13-yl 6-mercaptohexanoate.
62. Rhizoxin-13-yl 6-(ethyldithio)hexanoate.
63. Rhizoxin-13-yl 6,6'-dithiodihexanonate.
64. Rhizoxin-13-yl 6-(acetylthio)hexanoate.
65. Rhizoxin-13-yl 6-(isovalerylthio)hexanoate.
66. Rhizoxin-13-yl 6-(heptanoylthio)hexanoate.
67. Rhizoxin-13-yl 6-(nonanoylthio)hexanoate.
68. Rhizoxin-13-yl 6-(undecanoylthio)hexanoate.

69. Rhizoxin-13-yl 6-(palmitoylthio)hexanoate.
70. Rhizoxin-13-yl 12-mercaptododecanoate.
71. Rhizoxin-13-yl 12-(ethyldithio)dodecanoate.
72. Rhizoxin-13-yl 12-(propionylthio)dodecanoate.
73. Rhizoxin-13-yl 12-(valerylthio)dodecanoate.
74. Rhizoxin-13-yl 12-(decanoylthio)dodecanoate.
75. Rhizoxin-13-yl 16-(docosanoylthio)hexadecanoate.
76. Rhizoxin-13-yl 12-(ethoxyphosphonooxy)dodecanoate.
77. Rhizoxin-13-yl aminoacetate.
78. Rhizoxin-13-yl 2,2,2-trichloroethoxycarbonylaminoacetate.
79. Rhizoxin-13-yl acetamidoacetate.
80. Rhizoxin-13-yl pivaloylaminoacetate.
81. Rhizoxin-13-yl phosphonoaminoacetate.
82. Rhizoxin-13-yl (sec-butoxyphosphonoamino)acetate.
83. Rhizoxin-13-yl 3-aminopropionate.
84. Rhizoxin-13-yl 3-(methylamino)propionate.
85. Rhizoxin-13-yl 3-(diethylamino)propionate.
86. Rhizoxin-13-yl 3-(N-ethyl-N-methylamino)propionate.
87. Rhizoxin-13-yl 3-(2,2,2-trichloroethoxycarbonylamino)propionate.
88. Rhizoxin-13-yl 3-(benxyloxycarbonylamino)propionate.
89. Rhizoxin-13-yl 3-(t-butoxycarbonylamino)propionate.
90. Rhizoxin-13-yl 3-(hexanoylamino)propionate.
91. Rhizoxin-13-yl 3-(decanoylamino)propionate.
92. Rhizoxin-13-yl 3-(lauroylamino)propionate.
93. Rhizoxin-13-yl 3-(myristoylamino)propionate.
94. Rhizoxin-13-yl 3-(docosanoylamino)propionate.
95. Rhizoxin-13-yl 3-[P-propoxy-P-(2,2,2-trichloroethoxy)phosphonoamino]propionate.
96. Rhizoxin-13-yl 3-[P-decyloxy-P-(2,2,2-trichloroethoxy)phosphonoamino]propionate.
97. Rhizoxin-13-yl 3-(decyloxyphosphonoamino]propionate.
98. Rhizoxin-13-yl 6-aminohexanoate.
99. Rhizoxin-13-yl 6-(methylamino)hexanoate.
100. Rhizoxin-13-yl 6-(diethylamino)hexanoate.
101. Rhizoxin-13-yl 6-(N-ethyl-N-methylamino)hexanoate.
102. Rhizoxin-13-yl 6-(2,2,2-trichloroethoxycarbonylamino)hexanoate.
103. Rhizoxin-13-yl 6-acetamidohexanoate.
104. Rhizoxin-13-yl 6-(4-methylvalerylamino)hexanoate.
105. Rhizoxin-13-yl 6-heptanoylaminohexanoate.
106. Rhizoxin-13-yl 6-nonanoylaminohexanoate.
107. Rhizoxin-13-yl 6-undecanoylaminohexanoate.
108. Rhizoxin-13-yl 6-docosanoylaminohexanoate.
109. Rhizoxin-13-yl 6-(P-hexyloxyphosphonoamino)hexanoate.
110. Rhizoxin-13-yl 6-(P-decyloxyphosphonoamino)hexanoate.
111. Rhizoxin-13-yl 12-aminododecanoate.
112. Rhizoxin-13-yl 12-(ethylamino)dodecanoate.
113. Rhizoxin-13-yl 12-(diethylamino)dodecanoate.
114. Rhizoxin-13-yl 12-(2,2,2-trichloroethoxycarbonylamino)dodecanoate.
115. Rhizoxin-13-yl 12-propionamidododecanoate.
116. Rhizoxin-13-yl 12-valeramidododecanoate.
117. Rhizoxin-13-yl 12-(tridecanoylamino)dodecanoate.
118. Rhizoxin-13-yl 12-(docosanoylamino)dodecanoate.
119. Rhizoxin-13-yl 12-(P-ethoxyphosphonoamino)dodecanoate.
120. Rhizoxin-13-yl 12-(P-decyloxyphosphonoamino)dodecanoate.
121. Rhizoxin-13-yl 20-aminoicosanoate.
122. Rhizoxin-13-yl 20-(2,2,2-trichloroethoxycarbonylamino)icosanoate.
123. Rhizoxin-13-yl 20-butyroylaminoicosanoate.
124. Rhizoxin-13-yl 20-heptanoylaminoicosanoate.
125. Rhizoxin-13-yl 20-myristoylaminoicosanoate.
126. Rhizoxin-13-yl 20-phosphonoaminoicosanoate.
127. Rhizoxin-13-yl 20-(P-butoxyphosphonoamino)icosanoate.
128. Rhizoxin-13-yl 3-nonyloxycarbonylpropionate.
129. Rhizoxin-13-yl 3-undecyloxycarbonylpropionate.
130. Rhizoxin-13-yl 3-tridecyloxycarbonylpropionate.
131. Rhizoxin-13-yl 5-hexyloxycarbonylvalerate.
132. Rhizoxin-13-yl 5-nonyloxycarbonylvalerate.
133. Rhizoxin-13-yl 5-hexadecyloxycarbonylvalerate.
134. Rhizoxin-13-yl 15-methoxycarbonylpentadecanoate.
135. Rhizoxin-13-yl 15-hexyloxycarbonylpentadecanoate.
136. Rhizoxin-13-yl 15-pentadecyloxycarbonylpentadecanoate.
137. Rhizoxin-13-yl 15-nonadecyloxycarbonylpentadecanoate.
138. Rhizoxin-13-yl 3-(methylthio)propionate.
139. Rhizoxin-13-yl 3-(ethylthio)propionate.
140. Rhizoxin-13-yl 3-(hexylthio)propionate.
141. Rhizoxin-13-yl 3-(isopentylthio)propionate.
142. Rhizoxin-13-yl 3-(nonylthio)propionate.
143. Rhizoxin-13-yl 3-(cyclohexylthio)propionate.
144. Rhizoxin-13-yl 3-(decylthio)propionate.
145. Rhizoxin-13-yl 3-(2-hydroxyethylthio)propionate.
146. Rhizoxin-13-yl 3-(5-methoxypentylthio)propionate.
147. Rhizoxin-13-yl 3-(5-hydroxypentylthio)propionate.
148. Rhizoxin-13-yl 3-(2-aminoethylthio)propionate.
149. Rhizoxin-13-yl 3-[2-(methylamino)ethylthio]propionate.
150. Rhizoxin-13-yl 3-(2-mercaptoethylthio)propionate.
151. Rhizoxin-13-yl 3-(5-methylthiopentylthio)propionate.
152. Rhizoxin-13-yl 3-(2-carboxyethylthio)propionate.
153. Rhizoxin-13-yl 3-(5-methoxycarbonylpentylthio)propionate.
154. Rhizoxin-13-yl 3-(10-hydroxydecylthio)propionate.
155. Rhizoxin-13-yl 3-(10-aminodecylthio)propionate.
156. Rhizoxin-13-yl 3-(10-mercaptodecylthio)propionate.
157. Rhizoxin-13-yl 3-(10-methoxycarbonyldecylthio)propionate.
158. Rhizoxin-13-yl 3-(phenethylthio)propionate.
159. Rhizoxin-13-yl 3-($\beta$-naphthylmethylthio)propionate.
160. Rhizoxin-13-yl 3-(4-methoxybenzhydrylthio)propionate.

161. Rhizoxin-13-yl 3-(2-furylthio)propionate.
162. Rhizoxin-13-yl 3-(2-thienylthio)propionate.
163. Rhizoxin-13-yl 3-(5-amino-2-thienylthio)propionate.
164. Rhizoxin-13-yl 3-(2-pyridylthio)propionate.
165. Rhizoxin-13-yl 3-(2-guinolylthio)propionate.
166. Rhizoxin-13-yl 3-(4-piperidylthio)propionate.
167. Rhizoxin-13-yl 6-(ethylthio)hexanoate.
168. Rhizoxin-13-yl 6-(hexylthio)hexanoate.
169. Rhizoxin-13-yl 6-(cyclohexylthio)hexanoate.
170. Rhizoxin-13-yl 6-(5-hydroxypentylthio)hexanoate.
171. Rhizoxin-13-yl 6-[2-(dimethylamino)ethylthio]-hexanoate.
172. Rhizoxin-13-yl 6-(2-propylthioethylthio)hexanoate.
173. Rhizoxin-13-yl 6-(5-carbamoylpentylthio)hexanoate.
174. Rhizoxin-13-yl 12-(methylthio)dodecanoate.
175. Rhizoxin-13-yl 12-(propylthio)dodecanoate.
176. Rhizoxin-13-yl 12-(undecylthio)dodecanoate.
177. Rhizoxin-13-yl 12-(3-methylpentylthio)-dodecanoate.
178. Rhizoxin-13-yl 12-(5-hydroxypentylthio)-dodecanoate.
179. Rhizoxin-13-yl 12-(5-phosphonooxypentylthio)-dodecanoate.
180. Rhizoxin-13-yl 12-(2-methoxyethylthio)-dodecanoate.
181. Rhizoxin-13-yl 12-(5-aminopentylthio)-dodecanoate.
182. Rhizoxin-13-yl 12-(11-aminoundecylthio)-dodecanoate.
183. Rhizoxin-13-yl 12-[2-(methylthiocarbonyl)ethyl-thio]dodecanoate.

All of the above compounds are shown in the form of the ring-closed lactone. It will, of course, be understood that each of the above compounds can also exist in the form of a ring-opened acid and that such acids can form salts and esters, and the acids and their corresponding salts and esters of the above compounds are also preferred. Of the compounds listed above, the following are particularly preferred, that is to say Compounds No. 1, 2, 3, 7, 8, 9, 11, 13, 15, 18, 22, 24, 27, 28, 29, 30, 31, 32, 34, 36, 38, 41, 43, 45, 46, 47, 49, 50, 51, 56, 57, 58, 61, 63, 66, 67, 68, 70.73, 74, 77, 83, 84, 85, 86, 87, 88, 89, 90, 91, 92, 93, 94, 95, 96, 97, 98, 100, 101, 102, 103, 104, 105, 106, 107, 108, 109, 110, 111, 113, 114, 115, 116, 117, 121, 123, 124, 128, 129, 130, 132, 133, 138, 145, 147, 148, 151, 157, 162, 164, 167, 171, 173, 174, 178, 182 and 183, whilst Compounds No. 1, 7, 11, 13, 15, 18, 22, 27, 28, 31, 32, 34, 38, 41, 43, 45, 47, 49, 50, 51, 56, 57, 58, 63, 77, 83, 85, 87, 88, 89, 90, 91, 92, 93, 94, 98, 102, 104, 105, 106, 107, 109, 110, 111, 115, 116, 121, 128, 129, 130, 138, 145, 148, 151, 167, 171, 173, 174, 182 and 183 are more preferred.

The most preferred compounds are Compounds No. 27, 31, 32, 49, 50, 51, 57, 83, 91, 98, 102, 107, 111 and 116, as defined above, and pharmaceutically acceptable salts and esters thereof.

The compounds of the present invention can, in principle, be prepared by simple acylation of rhizoxin, which has the formula (A) given above, with an acid of formula $R(CH_2)_nCOOH$ or with a reactive derivative thereof, and then, if required, converting any resulting group represented by R to any other such group. In more detail, they may be prepared as illustrated by the following reaction scheme:

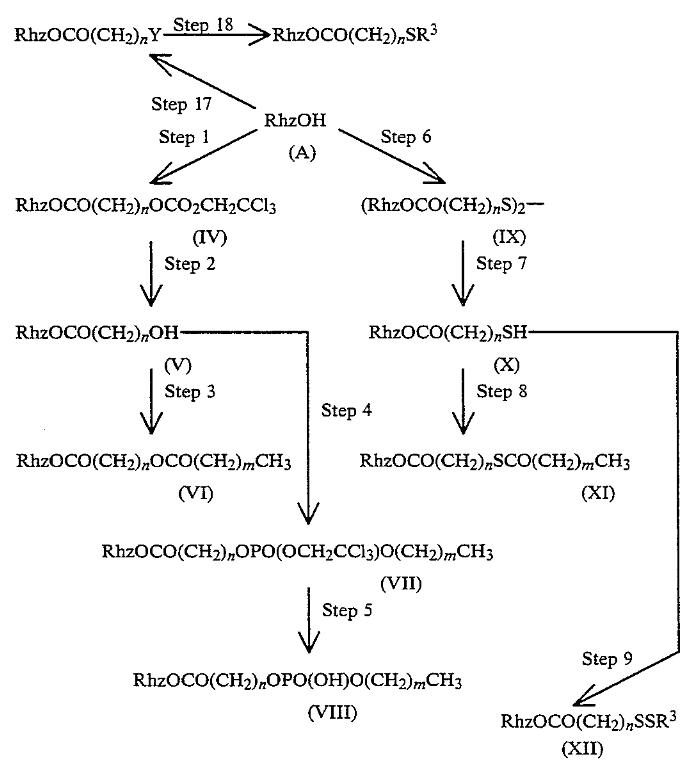

(A) (IV) (IX) (V) (X) (VI) (XI) (VII) (VIII) (XII)

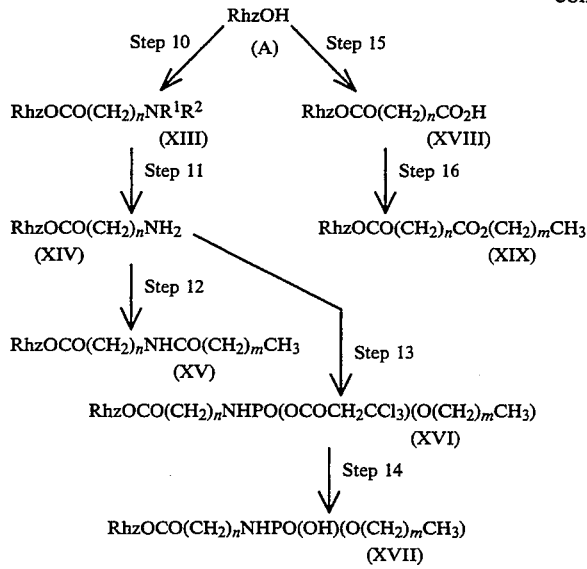

In the above formulae, R, $R^1$, $R^2$ and n are as defined above, m represents an integer from 1 to 25, and $R^3$ represents an alkyl group having from 1 to 25 carbon atoms which is unsubstituted or has at least one substituent selected from the group consisting of substituents (a), defined above, for example a methyl, ethyl or propyl group, or an aralkyl group in which the alkyl part has from 1 to 4 carbon atoms and the aryl part is a $C_6$–$C_{10}$ carbocyclic aryl group which is unsubstituted or has at least one substituent selected from the group consisting of substituents (b), defined above, for example a benzyl, phenethyl or phenylpropyl (1-, 2- or 3-) group.

Many of the steps involved in these reactions are similar, and these are described below.

(i) Esterification process

This is involved in Steps 1, 6, 10, 15, 16 and 17.

This process forms an ester linkage between the hydroxy group at the 13-position of rhizoxin (A), by reacting the rhizoxin with a carboxylic acid of formula $Cl_3CCH_2OOCO(CH_2)_nCOOH$ or with a reactive derivative thereof, such as an acid anhydride. The reaction is preferably effected in the presence of an acid binding agent and, especially when the free acid is used, in the presence of a condensing agent. Where an acid binding agent is employed, its nature is not critical and any such compound may be employed, provided that it does not interfere with the reaction or with other parts of the rhizoxin molecule. Examples include such alkalis as alkali metal carbonates (e.g. sodium carbonate or potassium carbonate) and alkali metal bicarbonates (e.g. sodium bicarbonate) and such organic amines as triethylamine, pyridine, dimethylaminopyridine or pyrrolidinopyridine. Examples of condensing agents which may be used in these steps include DCC (dicyclohexylcarbodiimide), CDI (N,N'-carbonyldiimidazole), DPPA (diphenylphosphoryl azide), HOBT (1-hydroxybenzotriazole), HONB (N-hydroxy-5-norbornene-2,3-dicarboxyimide) and EDAPC [1-ethyl-3-(3-dimethylaminopropyl)carbodiimide]. When pyridine, dimethylaminopyridine or pyrrolidinopyridine is employed, the reaction proceeds more rapidly. The reaction is normally and preferably effected in the presence of a solvent. There is no particular restriction on the nature of the solvent to be employed, provided that it has no adverse effect on the reaction or on the reagents involved. Examples of suitable solvents include: halogenated hydrocarbons, especially halogenated aliphatic hydrocarbons, such as methylene chloride, chloroform and dichloroethane; and aromatic hydrocarbons, such as benzene, toluene and xylene. The reaction can take place over a wide range of temperatures, and the precise reaction temperature is not critical to the invention. In general, we find it convenient to carry out the reaction at a temperature from 100° C. and 0° C., but usually at room temperature. The time required for the reaction may also vary widely, depending on many factors, notably the reaction temperature and the nature of the reagents. However, provided that the reaction is effected under the preferred conditions outlined above, a period of from 10 minutes to 48 hours will usually suffice, depending upon the reaction temperature: for example, when the reaction is carried out at room temperature, it will normally be complete in 3 hours.

(ii) Removal of trichloroethyl group

This occurs in Steps 2, 5, 11 and 14.

In this step, a trichloroethyl group is removed from the trichloroethoxycarbonyloxy group [the compound of formula (IV), prepared in Step 1], the trichloroethoxycarbonylamino group [which may be one of the groups represented by $R^1$ or $R^2$ in the compound of formula (XIII), prepared in Step 10] and the trichloroethylphosphoryl group [in the compound of formula (VII), prepared in Step 4, or the compound of formula (XVI), prepared in Step 13], to form a free hydroxy group, an amino group or a phosphoryl group, respectively. This type of reaction is well known in the art, and the nature of the reagents to be used is not particularly critical, provided that they can remove the trichloroethyl group, without affecting other parts of the molecule of the compound of formula (IV), (VII), (XIII) or (XVI). Zinc dust is preferred. The reaction is normally and preferably effected in the presence of a solvent. There is no particular restriction on the nature of the solvent to be employed, provided that it has no adverse effect on the reaction or on the reagents involved. Examples of suitable solvents include: alcohols, such as methanol and ethanol; organic acids, especially organic carboxylic acids, and preferably aqueous acids, such as aqueous formic acid and acetic acid; and mixtures of an aqueous solution (which has been adjusted a pH of from 1 to 8) with an organic solvent, such as an ether (e.g. tetrahydrofuran or dioxane), a ketone (e.g. acetone) or an ester (e.g. ethyl acetate). The reaction can take place over a wide range of temperatures, and the precise reaction temperature is not critical to the invention. In general, we find it convenient to carry out the reaction at a temperature from 100° C. and 0° C. The time required for the reaction may also vary widely, depending on many factors, notably the reaction temperature and other reaction conditions (mainly the nature of the solvent) and the nature of the reagents. However, provided that the reaction is effected under the preferred conditions outlined above, a period of from 10 minutes and 50 hours will usually suffice, depending upon the reaction solvent used. When a mixture of a phosphate buffer and tetrahydrofuran having a pH of 4.2 is used, the reaction is preferably carried out at room temperature for 3 hours, with stirring.

(iii) Reduction of disulfide

This occurs in Step 7.

In this step, the disulfide of an acylated rhizoxin of formula (IX), prepared in Step 6, is reduced, to form an acylated rhizoxin derivative of formula (X) having a mercapto group on the terminal acyl group. The reaction is normally and preferably effected in the presence of a solvent. The reagents and reaction solvents to be used are not particularly critical, provided that they can reduce the disulfide linkage to a mercapto group. Examples are essentially as given for Step (ii). However, again we prefer to use zinc dust together with, as the reaction solvent, a mixture of a buffer adjusted a pH of from 1 to 7 and an organic solvent such as tetrahydrofuran or acetone. The reaction can take place over a wide range of temperatures, and the precise reaction temperature is not critical to the invention. In general, we find it convenient to carry out the reaction at a temperature from 100° C. to 0° C. The time required for the reaction may also vary widely, depending on many factors, notably the reaction temperature and the nature of the reagents. However, provided that the reaction is effected under the preferred conditions outlined above, a period of from 1 to 5 hours will usually suffice. For example, if the reaction is carried out at room temperature, it will normally be complete in 3 hours.

(iv) Acylation process

This is involved in Steps 3, 8 and 12.

In this Step an acylated rhizoxin derivative having a hydroxy group, a mercapto or an amino group at the terminal position of the acyl group is further acylated by reacting it with a carboxylic acid or with an active derivative thereof. Any active derivative of a carboxylic acid commonly used in this type of reaction may equally be used here, as is well known to those skilled in the art. Examples include carboxylic acid chlorides and carboxylic acid bromides. It is also possible to use the carboxylic acid itself, but, in this case, it is also highly desirable to carry out the reaction in the presence of a condensing agent, such as DCC and the like, as described in Step (i), "Esterification process", above. In order to accelerate the reaction, it is possible to use an organic base, for example pyridine, dimethylaminopyridine or pyrrolidinopyridine, as a catalyst. The reaction is normally and preferably effected in the presence of a solvent. There is no particular restriction on the nature of the solvent to be employed, provided that it has no adverse effect on the reaction or on the reagents involved. Examples of suitable solvents include: halogenated hydrocarbons, especially halogenated aliphatic hydrocarbons, such as methylene chloride, chloroform or dichloroethane; and aromatic hydrocarbons, such as benzene, toluene and xylene. The reaction can take place over a wide range of temperatures, and the precise reaction temperature is not critical to the invention. In general, we find it convenient to carry out the reaction at a temperature from 80° C. to −30° C. although this depends on the reagents used. The time required for the reaction may also vary widely, depending on many factors, notably the reaction temperature and the nature of the reagents. For example, when an acid halide is employed, the reaction will usually be complete within a period of from 1 to 10 hours at 0° C.; whereas, when a condensing agent such as DCC is employed, it will usually be complete within a period of from 1 to 10 hours at room temperature.

(v) Phosphorylation process

This is employed in Steps 4 and 13.

In this step, an acylated rhizoxin derivative of formula (V) or (XIV) having a hydroxy group or an amino group, respectively, at the terminal position of the acyl chain is phosphorylated by reacting it with an activated phosphoric acid derivative. Examples of suitable activated phosphoric acid derivatives include phosphoric acid halides, such as P-substituted phosphorochloridates, which are preferably reacted in the presence of an acid binding agent, and P-substituted phosphoric acid derivatives, which are preferably reacted in the presence of a condensing agent such as DCC. The reaction is normally and preferably effected in the presence of a solvent. There is no particular restriction on the nature of the solvent to be employed, provided that it has no adverse effect on the reaction or on the reagents involved. Examples of suitable solvents include: aromatic hydrocarbons, such as benzene and toluene: halogenated hydrocarbons, especially halogenated aliphatic hydrocarbons, such as methylene chloride, chloroform and dichloroethane; amides, especially fatty acid amides, such as dimethylacetamide and dimethylformamide; phosphoric acid amides, such as hexamethylphosphoric triamide; and phosphoric acid triesters, such as trimethyl phosphate and triethyl phosphate. There is also no particular limitation on the nature of the acid binding agent to be used, and any such compound commonly used in reactions of this type may equally be used here. Examples include tertiary amines, such as triethylamine, tripropylamine and tributylamine, as well as pyridines, such as pyridine, dimethylaminopyridine and 4-pyrrolidinopyridine. The reaction can take place over a wide range of temperatures, and the precise reaction temperature is not critical to the invention, although the preferred temperature depends on the reagent and acid binding agent to be used. In general, we find it convenient to carry out the reaction at a temperature from 80° C. to 0° C., most preferably around room temperature. The time required for the reaction may also vary widely, depending on many factors, notably the reaction temperature and the nature of the reagents. However, provided that the reaction is effected under the preferred conditions outlined above, a period of from 3 to 15 hours will usually suffice.

(vi) Disulfide formation

This is involved in Step 9.

In this Step, an acylated rhizoxin of formula (X) having a sulfhydryl group at the terminal position is reacted with another compound having a sulfhydryl group to afford an acylated rhizoxin of formula (XII) having an asymmetric disulfide linkage. There is no particular restriction on the nature of the reagents to be used for forming the asymmetric disulfide linkage in this step, and 2,4-dinitrobenxenesulphenyl chloride is preferably used. The reaction is normally and preferably effected in the presence of a solvent. There is no particular restriction on the nature of the solvent to be employed, provided that it has no adverse effect on the reaction or on the reagents involved. Examples of suitable solvents include: nitriles, such as acetonitrile; ketones, such as acetone; and amides, such as dimethylformamide. The reaction can take place over a wide range of temperatures, and the precise reaction temperature is not critical to the invention. In general, we find it convenient to carry out the reaction at a temperature from 100° C. to −20° C., and usually at from 0° C. to room temperature. The time required for the reaction may also vary widely, depending on many factors, notably the reaction temperature and the nature of the reagents. However, provided that the reaction is effected under the preferred conditions outlined above, and at from 0° C. to room temperature, a period of from 1 to 24 hours will usually suffice.

(vii) Sulfide formation

This Step is involved in Step 18.

In this an acylated rhizoxin derivative having terminal halogen atoms is reacted with a mercaptan to form a corresponding sulfide bond. In order to accelerate the reaction, the mercaptan may be employed in the form of a metal salt thereof (which may be prepared by reacting the mercaptan with, for example, a silver salt such as silver perchlorate, silver acetate or silver carbonate). The reaction is preferably effected in the presence of a solvent. There is no particular restriction on the nature of the solvent to be employed, provided that it has no adverse effect on the reaction or on the reagents involved. Examples of suitable solvents include: nitriles, such as acetonitrile. The reaction can take place over a wide range of temperatures, and the precise reaction temperature is not critical to the invention. In general, we find it convenient to carry out the reaction at a temperature from −30° C. to 80° C. The time required for the reaction may also vary widely, depending on many factors, notably, the reaction temperature and the nature of the reagents. However, provided that the reaction is effected under the preferred conditions outlined above, a period of from 1 to 100 hours will usually suffice.

In the reaction scheme shown and discussed above, the group shown as Rhz may be replaced by the corresponding group derived from rhizoxin-2-ene, to prepare the corresponding rhizoxin-2-ene derivatives. In this case, the starting material for the reaction scheme is rhizoxin-2-ene, which may be prepared as disclosed in the 1984 International Chemical Congress of the Pacific Basin Society, Honolulu, Hi.

The product of the reactions shown above is the lactone of formula (I). Pharmaceutically acceptable salts of the carboxylic acid of formula (III) can be prepared by reacting this lactone of formula (I) with a base. This is a conventional reaction for forming a salt from a lactone and may be carried out using techniques well-known in the art.

For example, metal salts of the carboxylic acid of formula (III) can be prepared by reacting the lactone of formula (I) with a hydroxide or carbonate of the appropriate metal, preferably in an aqueous solvent. The nature of this solvent is not critical, provided that it has no adverse effect upon the reaction. Suitable solvents include water itself and mixtures of water with one or more organic solvents, for example: an alcohol, such as methanol or ethanol: an ether, such as ethylene glycol dimethyl ether or dioxane; a ketone, such as acetone; or another solvent such as hexane, ethyl acetate, dimethylformamide, dimethyl sulfoxide or pyridine. A mixture of a hydrophilic organic solvent with water is particularly preferred. The reaction temperature is not critical and we therefore normally prefer to carry out the reaction at about room temperature. However, if desired, it may be conducted whilst gently heating.

In order to avoid opening the lactone formed between the carbon atoms at positions 15 and 1, it is preferred that the ring-opening reaction should take place under relatively mild conditions, e.g. using a relatively dilute solution of the base and/or at relatively low temperatures, e.g. around room temperature.

An amine salt of the carboxylic acid of formula (III) may be prepared by reacting the lactone of formula (I) with an amine, preferably in an aqueous solvent. The solvent employed is not critical, provided that it has no adverse effect upon the reaction. Suitable solvents include water itself and mixtures of water with one or more organic solvents, for example: an alcohol, such as methanol or ethanol; an ether, such as tetrahydrofuran; a nitrile, such as acetonitrile; or a ketone, such as acetone. The preferred solvent is aqueous acetone. The reaction is preferably effected at a pH value of from 7 to 8.5 and, although the reaction temperature is not particularly critical, we prefer a relatively low temperature in order to avoid side reactions. Accordingly, the temperature is preferably below room temperature, more preferably from 5° to 10° C. The reaction goes immediately to completion. The amine salt may also be produced by a salt-exchange reaction, that is to say by adding a mineral acid salt (e.g. the hydrochloride) of the desired amine to an aqueous solution of an metal salt of the compound of formula (III).

An amino acid salt of the carboxylic acid of formula (III) can be prepared by contacting the lactone of formula (I) with an appropriate amino acid, preferably in an aqueous solvent. The solvent employed is not critical, provided that it has no adverse effect upon the reaction. Suitable solvents are aqueous solvents, such as water itself and mixtures of water with one or more organic solvents, for example: an alcohol, such as methanol or ethanol; or an ether, such as tetrahydrofuran. The reaction temperature is not critical, but best results are obtained by heating the reagents, preferably at a temperature of from 50° to 60° C.

The free acids of formula (III) can be prepared by contacting a salt thereof with an acid. The reaction may be carried out by conventional means, as are well-known in this art. For example, the reaction is preferably effected in the presence of a solvent, the nature of which is not critical, provided that it has no adverse effect upon the reaction. Suitable solvents include, for example: alcohols, such as methanol; ketones, such as acetone; and amides, such as dimethylformamide or dimethylacetamide. The salt of the carboxylic acid of formula (III) is dissolved in such a solvent, and then a stoichiometric equivalent or a slight excess of an acid is added. There is no particular limitation on the nature of the acid to be used and any organic or inorganic acid may be employed, provided that it does not have any adverse effect upon the desired compound. Suitable acids include trifluoroacetic acid, hydrochloric acid and sulfuric acid.

The resulting compounds of the invention, prepared by any of the methods described above, can be recovered from the reaction mixtures and, if desired, further purified by any conventional technique or by a combination of such techniques. For example, one suitable recovery procedure comprises: pouring the reaction mixture into water; extracting the product with a water-immiscible solvent, such as benzene, diethyl ether or ethyl acetate; and then evaporating off the solvent, if necessary after drying the extract, to afford the desired compound. This may, if desired, be purified by an adsorption chromatography technique, using an adsorbent such as activated carbon or silica gel, by ion-exchange chromatography, by gel filtration with a suitable adsorbent, such as Sephadex (trade mark) or by recrystallization from an organic solvent, such as diethyl ether, ethyl acetate or chloroform. Of course, a combination of these techniques may be employed, if appropriate.

The rhizoxin derivatives of the present invention exhibited a stronger anti-tumor activity against p-388 cell tumors which were transplanted to a mouse than did the compounds described in U.S. Pat. No. 4,791,128.

The rhizoxin derivatives of the present invention can be used as anti-tumor agents for the treatment of neoplastic diseases of homoiothermic animals, especially mammals, including humans. The compounds may be administered by any suitable route, for example the parenteral route (e.g. by intravenous, subcutaneous or intramuscular injection) or by suppository, or by the oral route (for example in the form of a tablet, capsule, powder or granule).

If desired, the compound of the invention may be administered as such, but it is preferably employed in association with a conventional pharmaceutically acceptable carrier or diluent, appropriate to the particular route of administration.

For example, the composition may contain suspending agents, stablizing agents or dispersing agents and it may be provided as a powder which, prior to administration, is dissolved in a suitable solvent, for example a pyrogen-free sterilized aqueous solvent. Such a powdered preparation may, for example, be produced by pipetting an acetone solution of the compound into a vial, adding water thereto and then lyopholizing the mixture. Compositions for oral use may be provided as tablets, capsules, powders, granules or syrups containing an appropriate amount of the compound of the invention.

Compositions for injection are preferably provided as an ampoule containing a unit dose or as a vial containing multiple doses.

If desired, the compounds of the invention may be used together with one or more other anti-cancer agents, for example drugs of the nitrosourea series, such as ACNU or BCNU, cisplastin, 5-FU, daunomycin, adriamycin, mitomycin C or etoposide.

The dosage of the compounds of the invention will vary, depending upon the severity and nature of the disease, as well as the route, frequency and period of administration. However, a suitable dose for an adult human would be in the range of from 1 to 100 mg per day, which may be administered in a single dose or in divided doses.

The preparation of the compounds of the present invention is further illustrated by the following non-limiting Examples. The preparation of certain starting materials used in the preparation of the compounds of the invention is illustrated by the subsequent Preparations.

EXAMPLE 1

Rhizoxin-13-yl 12-(2,2,2-trichloroethoxycarbonyloxy)dodecanoate $Rhz-OOC(CH_2)_{11}OCOOCH_2CCl_3$ 3.12 g of rhizoxin and 4.30 g of 12-(2,2,2-trichloroethoxycarbonyloxy)dodecanoic acid (prepared as described in Preparation 2) were dissolved in methylene chloride. 4.12 g of DCC (N,N-dicyclohexylcarbodiimide) and a catalytic amount of 4-pyrrolidinopyridine were then added to the resulting solution, which was then stirred for about 3 hours. At the end of this time, the methylene chloride was removed by evaporation under reduced pressure, and ethyl acetate was added to the residue. The resulting mixture was then washed with 0.2N aqueous hydrochloric acid, with a saturated aqueous solution of sodium bicarbonate and with water, in that order. The resulting mixture was dried over anhydrous magnesium sulfate, and the solvent was removed by evaporation under reduced pressure. The residue was purified by column chromatography through silica gel, using a 1:1 by volume mixture of cyclohexane and ethyl acetate as eluent, to afford 4.62 g of the title compound.

Nuclear Magnetic Resonance Spectrum (270 MHz in $CDCl_3$) δ ppm: 4.79 (2H, singlet); 4.26 (1H, doublet of doublets, J=10.3 & 4.6 Hz); 4.24 (2H, triplet, J=6.5 Hz); 1.24–1.45 (18H, broad singlet).

EXAMPLE 2

Rhizoxin-13-yl 12-hydroxydodecanoate $Rhz-OOC(CH_2)_{11}OH$ 4.26 g of rhizoxin-13-yl 12-(2,2,2-trichloroethoxycarbonyloxy)dodecanoate (prepared as described in Example 1) were dissolved in acetone, and a 1M aqueous solution of sodium phosphate was added to the resulting solution, which was then vigorously agitated. 10 g of zinc dust were added to the resulting mixture and the mixture was stirred for about 2 hours. At the end of this time, insolubles were removed by filtration and the solvent was removed by evaporation under reduced pressure. Ethyl acetate and water were added to the residue to effect separation, and the ethyl acetate layer was washed with a saturated aqueous solution of sodium bicarbonate and with water, after which the mixture was dried over anhydrous magnesium sulfate, and then the solvent was removed by evaporation under reduced pressure. The residue was purified by column chromatography through silica gel, using a 99.5:0.5 by volume mixture of methylene chloride and methanol as eluent, to afford 730 mg of the title compound.

Nuclear Magnetic Resonance Spectrum (270 MHz in $CDCl_3$) δ ppm: 4.25 (1H, quartet, J=10.3 & 4.6 Hz);

3.64 (2H, triplet, J=6.5 Hz); 2.30–2.41 (2H, multiplet); 1.50–1.85 (2H, multiplet); 1.24–1.42 (16H, broad singlet).

EXAMPLE 3

Rhizoxin-13-yl 12-(propionyloxy)dodecanoate

Rhz—OOC(CH$_2$)$_{

Nuclear Magnetic Resonance Spectrum (270 MHz in CDCl$_3$) δ ppm; 4.27 (1H, doublet of doublets, J=10.8 & 3.8 Hz); 2.70 (2H, triplet J=7.0 Hz); 2.57 (2H, triplet J=7.0 Hz); 1.45 (4H, broad singlet); 1.26 (12H, broad singlet); 0.88 (3H, triplet J=6.8 Hz)

EXAMPLE 10

Rhizoxin-13-yl 3-(myristoylthio)propionate

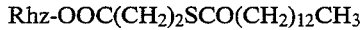
Rhz-OOC(CH$_2$)$_2$SCO(CH$_2$)$_{12}$CH$_3$

The reaction, treatment and purification steps were conducted in the same manner as described in Example 8, but using 90 mg of rhizoxin-13-yl 3-mercaptopropionate (prepared as described in Example 7), 109 mg of myristoyl chloride, 70 mg of pyridine and 5 mg of 4-dimethylaminopyridine (DMAP), to afford 57 mg of the title compound.

Nuclear Magnetic Resonance Spectrum (270 MHz in CDCl$_3$) δ ppm: 4.27 (1H, doublet of doublets, J=11.1 & 4.6 Hz); 2.71 (1H, triplet J=6.8 Hz); 2.57 (1H, triplet J=6.8 Hz); 1.61 (16H, broad singlet); 1.26 (4H, broad singlet); 0.88 (3H, triplet J=6.5 Hz).

EXAMPLE 11

Rhizoxin-13-yl 3-(2,2,2-trichloroethoxycarbonylamino)propionate

Rhz-OOC(CH$_2$)$_2$NHCOOCH$_2$CCl$_3$ 1.25 g of rhizoxin and 1.59 g of 3-(2,2,2-trichloroethoxycarbonylamino)propionic acid (prepared as described in Preparation 1) were dissolved in toluene, and 1.03 g of DCC was added to the resulting solution. A catalytic amount of 4-pyrrolidinopyridine was then added to the mixture, which was then stirred at room temperature for 2 hours. At the end of this time, ethyl acetate was added to the mixture, which was then washed with 0.1N aqueous hydrochloric acid, with a saturated aqueous solution of sodium bicarbonate and with water, in that order. The washed mixture was then dried over anhydrous magnesium sulfate, after which the solvent was removed by evaporation under reduced pressure. The residue was purified by column chromatography through silica gel, using a 1:1 by volume mixture of cyclohexane and ethyl acetate as eluent, to afford 1.25 g of the title compound.

Nuclear Magnetic Resonance Spectrum (270 MHz in CDCl$_3$) δ ppm: 5.68 (1H, broad singlet); 4.76 (2H, singlet); 4.32 (1H, doublet of doublets, J=11.1 & 3.2 Hz); 3.57 (2H, quartet, J=6.2 Hz); 2.66 (2H, triplet J=6.2 Hz).

EXAMPLE 12

Rhizoxin-13-yl 3-(benzyloxycarbonylamino)propionate

Rhz-OOC(CH$_2$)$_2$NHCOOCH C$_6$H$_5$

The reaction, treatment and purification steps were conducted in the same manner as described in Example 11 using 315 mg of rhizoxin and 560 mg of 3-(benzyloxycarbonylamino)propionic acid, to afford 415 mg of the title compound.

Nuclear Magnetic Resonance Spectrum (270 MHz in CDCl$_3$) δ ppm: 7.28-7.40 (5H, multiplet); 5.37 (1H, broad triplet, J=6.2 Hz); 5.11 (2H, triplet, J=12.5 Hz); 4.29 (1H, doublet of doublets, J=11.1 & 3.2 Hz); 3.53 (2H, quartet, J=6.2 Hz); 2.63 (2H, triplet, J=6.2 Hz).

EXAMPLE 13

Rhizoxin-13-yl 3-(t-butoxycarbonylamino)propionate

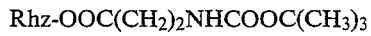
Rhz-OOC(CH$_2$)$_2$NHCOOC(CH$_3$)$_3$

The reaction, treatment and purification steps were conducted in the same manner as described in Example 11 using 315 mg of rhizoxin and 284 mg of 3-(t-butoxycarbonylamino)propionic acid, to afford 383 mg of the title compound.

Nuclear Magnetic Resonance Spectrum (270 MHz in CDCl$_3$) δ ppm: 5.08 (1H, broad singlet): 4.32 (1H, doublet of doublets, J=11.0 & 3.2 Hz); 3.45 (2H, quartet, J=6.2 & 6.2 Hz); 2.60 (2H, triplet, J=6.2 Hz); 1.44 (9H, singlet).

EXAMPLE 14

Rhizoxin-13-yl 3-aminopropionate

Rhz-OOC(CH$_2$)$_2$NH$_2$ 1.046 g of rhizoxin-13-yl 3-(2,2,2-trichloroethoxycarbonylamino)propionate (prepared as described in Example 11) was dissolved in 30 ml of tetrahydrofuran and 30 ml of a 1M aqueous solution of sodium phosphate was added to the resulting solution, followed by vigorous agitation. 5.0 g of zinc dust were added to the mixture in three portions every 30 minutes. After completion of the reaction, the zinc dust was removed by filtration and ethyl acetate was added for separation. The ethyl acetate layer was separated, washed with a saturated aqueous solution of sodium bicarbonate and with water, in that order, and then the solvent was removed by evaporation lander reduced pressure. The residue was purified by column chromatography, through silica gel, using a 90:10 by volume mixture of methylene chloride and ethanol as eluent, to afford 635 mg of the title compound.

Nuclear Magnetic Resonance Spectrum (270 MHz in CDCl$_3$) δ ppm: 3.15-3.30 (2H, multiplet); 2.75 (2H, triplet, J=5.4 Hz).

EXAMPLE 15

Rhizoxin-13-yl 3-(decanoylamino)propionate

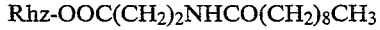
Rhz-OOC(CH$_2$)$_2$NHCO(CH$_2$)$_8$CH$_3$ 210 mg of rhizoxin-13-yl 3-aminopropionate and 155 mg of decanoic acid were dissolved in toluene, and then 155 mg of DCC and a catalytic amount of 4-pyrrolidinopyridine were added to the resulting solution, which was then stirred for about 2 hours. Treatment and purification were then conducted in the same manner as described in Example 1, to afford 160 mg of the title compound.

Nuclear Magnetic Resonance Spectrum (270 MHz in CDCl$_3$) δ ppm: 6.14 (1H, broad triplet, J=8.0 Hz); 4.31 (1H, doublet of doublets, J=11.1 & 3.2 Hz); 3.59 (2H, quartet, J=5.9 Hz); 2.60 (2H, triplet, J=5.9 Hz); 1.51-1.73 (4H, multiplet); 1.15-1.39 (12H, broad singlet); 0.88 (3H, triplet, J=4.6 Hz).

EXAMPLE 16

Rhizoxin-13-yl 3-(lauroylamino)propionate

Rhz-OOC(CH$_2$)$_2$NHCO(CH$_2$)$_{10}$CH$_3$ 270 mg of rhizoxin-13-yl 3-aminopropionate and 800 mg of lauric acid were dissolved in toluene, and 618 mg of DCC and then a catalytic amount of 4-pyrrolidinopyridine were added to the resulting solution, which was then stirred for about 2 hours. Treatment and purification were then conducted in the same manner as described in Example 15. to afford 192 mg of the title compound.

Nuclear Magnetic Resonance Spectrum (270 MHz in CDCl$_3$) δ ppm: 6.17 (1H, broad triplet, J=8.0 Hz); 4.32 (1H, doublet of doublets, J=11.1 & 3.2 Hz); 3.58 (2H, quartet, J=5.9 Hz); 2.60 (2H, triplet, J=7.6 Hz); 1.52–1.70 (2H, multiplet); 1.17–1.40 (16H, broad singlet); 0.88 (3H, triplet, J=4.6 Hz).

EXAMPLE 17

Rhizoxin-13-yl 3-(myristoylamino)propionate

Rhz-OOC(CH$_2$)$_2$NHCO(CH$_2$)$_{12}$CH$_3$ 275 mg of rhizoxin-13-yl 3-aminopropionate were dissolved in toluene, and 0.39 ml of myristoyl chloride was added to the resulting solution, which was then ice-cooled. 0.23 ml of triethylamine and a catalytic amount of DMAP were added to the cooled mixture, and the temperature of the mixture was allowed to return to room temperature, after which the mixture was stirred for 2 hours. At the end of this time, ethyl acetate was added to the resulting mixture, which was then washed with 1.1N aqueous hydrochloric acid and with water, in that order. The mixture was then dried over anhydrous magnesium sulfate, and the solvent was removed by evaporation under reduced pressure. The residue was purified by column chromatography through silica gel, using a 1:1 by volume mixture of cyclohexane and ethyl acetate as eluent, to afford 80 mg of the title compound.

Nuclear Magnetic Resonance Spectrum (270 MHz in CDCl$_3$) δ ppm: 6.17 (1H, broad triplet, J=8.1 Hz); 4.31 (1H, doublet of doublets, J=11.1 & 3.2 Hz); 3.58 (2H, quartet, J=5.9 Hz); 2.60 (2H, triplet, J=5.9 Hz); 2.34 (2H, triplet, J=8.9 Hz); 1.53–1.70 (2H, multiplet); 1.20–1.40 (20H, broad singlet); 0.88 (3H, triplet, J=6.8 Hz).

EXAMPLE 18

Rhizoxin-13-yl 3-(P-decyloxy-P-trichloroethoxyphosphonoamino)propionate

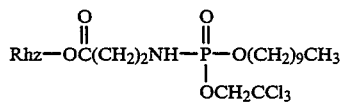
$$\text{Rhz}-\text{OC(CH}_2\text{)}_2\text{NH}-\overset{\overset{\text{O}}{\|}}{\underset{\underset{\text{OCH}_2\text{CCl}_3}{|}}{\text{P}}}-\text{O(CH}_2\text{)}_9\text{CH}_3$$

1.1 ml of decylalcohol were added to 15 ml of dry methylene chloride to prepare a solution, and then 1.4 ml of triethylamine were added to this solution. 1.33 g of trichloroethyl phosphotodichloridate was then added to the resulting mixture whilst stirring and ice-cooling, and then the stirring was continued at room temperature for 3 hours. At the end of this time, the mixture was ice-cooled, and 690 mg of rhizoxin-13-yl 3-aminopropionate (prepared as described in Example 14) were added, and stirring of the mixture was continued for a further 5 hours whilst removing the moisture. 30 ml each of methylene chloride and water were then added to the reaction mixture, and the mixture was stirred foe 30 minutes: the organic layer was then separated. This organic layer was washed with 20 ml each of 0.1N aqueous hydrochloric acid, of a saturated aqueous solution of sodium chloride and of a 5% w/v aqueous solution of sodium bicarbonate, after which it was dried over anhydrous magnesium sulfate. The solvent was then removed by evaporation under reduced pressure, to afford a caramel-like substance. This substance was dissolved in 20 ml of a 1:1 by volume mixture of cyclohexane and ethyl acetate and the solution was subjected to silica gel column chromatography through a column which had been saturated with the same solvents. It was eluted using a 2:1 by volume mixture of cyclohexane and ethyl acetate, and the main fractions were lyophilized from benzene, to afford 380 mg of the title compound as a yellow powder.

Nuclear Magnetic Resonance Spectrum (270 MHz in CDCl$_3$) δ ppm: 4.55 (1H, doublet, J=1.0 Hz); 4.53 (1H, doublet, J=1.0 Hz); 4.31 (1H, doublet of doublets, J=11.1 & 3.2 Hz); 4,09 (2H, quartet, J=5.9 Hz); 2.65 (2H, triplet, J=5.9 Hz); 1.15–1.43 (12H, broad singlet).

EXAMPLE 19

Sodium salt of rhizoxin-13-yl 3-(P-decyloxyphosphonoamino)propionate

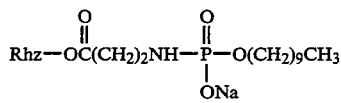
$$\text{Rhz}-\text{OC(CH}_2\text{)}_2\text{NH}-\overset{\overset{\text{O}}{\|}}{\underset{\underset{\text{ONa}}{|}}{\text{P}}}-\text{O(CH}_2\text{)}_9\text{CH}_3$$

272 mg of rhizoxin-13-yl 3-(P-decyloxy-P-trichloroethoxyphosphonoamino)propionate (prepared as described in Example 18) were dissolved in 27 ml of tetrahydrofuran, and 27 ml of sodium phosphate buffer (1 mole, pH: 4.2) were added to the resulting solution, after which 2.7 g of zinc dust were added, while agitating the mixture vigorously. The resulting mixture was then stirred at room temperature for 1 hour, after which the solvent was removed by evaporation under reduced pressure. 30 ml each of ethyl acetate and of a 5% w/v aqueous solution of sodium bicarbonate were added to the residue to dissolve it therein, and after insolubles had been removed by filtration, the organic layer was separated. The organic layer was washed with 20 ml each of 0.1N aqueous hydrochloric acid, of a saturated aqueous solution of sodium chloride and of a 5% w/v aqueous solution of sodium bicarbonate, and then it was dried over anhydrous magnesium sulfate. The desiccant was removed by filtration, and then the solvent was removed by evaporation under reduced pressure. The resulting residue was lyophilized from benzene, to afford 202 mg of the title compound as a yellow powder.

Nuclear Magnetic Resonance Spectrum (270 MHz in CDCl$_3$) δ ppm; 4.22 (1H, doublet of doublets, J=11.1 & 3.2 Hz); 3.73 (2H, broad doublet, J=5.9 Hz); 2.56 (2H, broad singlet); 1.12–1.48 (10H, broad singlet); 0.82 (3H, triplet, J=6.4 Hz).

EXAMPLE 20

Rhizoxin-13-yl 6-(2,2,2-trichloroethoxycarbonylamino)hexanoate

Rhz-OOC(CH$_2$)$_5$NHCOOCH$_2$CCl$_3$ 2.51 g of rhizoxin and 3.68 g of 6-(2,2,2-trichloroethoxycarbonylamino)hexanoic acid (prepared by a procedure similar to that described in Preparation 1) were dissolved in toluene, and 2.06 g of DCC, followed by a catalytic amount of 4-pyrrolidinopyridine, were added to the resulting solution, which was then stirred at room temperature for about 2 hours. Treatment and purification were then conducted in the same manner as described in Example 11, to afford 2.55 g of the title compound.

Nuclear Magnetic Resonance Spectrum (270 MHz in CDCl$_3$) δ ppm: 5.67 (1H, broad singlet); 4.71 (2H, singlet); 4.24 (1H, doublet or doublets, J=11.1 & 3.2 Hz); 3.15 (2H, multiplet); 2.30-2.45 (2H, multiplet).

EXAMPLE 21

Rhizoxin-13-yl 6-aminohexanoate.

Rhz-OOC(CH$_2$)$_5$NH$_2$ 2.95 g of rhizoxin-13-yl 6-(2,2,2-trichloroethoxycarbonylamino)hexanoate (prepared as described in Example 20) were dissolved in 60 ml or tetrahydrofuran, and 60 ml of a 1M aqueous solution of sodium phosphate were added to the resulting solution, followed by vigorous agitation. 10.0 g or zinc dust were added to the resulting mixture in three portions, once every hour. After 3 hours, treatment and purification were conducted in the same manner as described in Example 14, to afford 1.65 g of the title compound.

Nuclear Magnetic Resonance Spectrum (270 MHz in CDCl$_3$) δ ppm: 4.25 (1H, doublet or doublets, J=11.1 & 3.2 Hz); 2.96 (2H, triplet, J=5.4 Hz); 2.30-2.45 (2H, multiplet).

EXAMPLE 22

Rhizoxin-13-yl 6-(heptanoylamino)hexanoate

Rhz-OOC(CH$_2$)$_5$NHCO(CH$_2$)$_5$CH$_3$ 246 mg of rhizoxin-13-yl 6-aminohexanoate (prepared as described in Example 21) and 130 mg of heptanoic acid were dissolved in toluene, and 1.71 mg of DCC and a catalytic amount of 4-pyrrolidinopyridine were added to the resulting solution, which was then stirred at room temperature for about 2 hours. Treatment and purification were then conducted in the same manner as described in Example 1, to afford 187 mg of the title compound.

Nuclear Magnetic Resonance Spectrum (270 MHz in CDCl$_3$) δ ppm: 5.83 (1H, broad triplet, J=6.8 Hz); 4.28 (1H, doublet of doublets, J=10.8 & 3.8 Hz); 1.18-1.35 (8H, broad singlet); 0.89 (3H, triplet, J=6.8 Hz).

EXAMPLE 23

Rhizoxin-13-yl 6-(nonanoylamino)hexanoate

Rhz-OOC(CH$_2$)$_5$NHCO(CH$_2$)$_7$CH$_3$ 246 mg of rhizoxin-13-yl 6-aminohexanoate (prepared as described in Example 21) and 158 mg of nonanoic acid were dissolved in toluene, and 171 mg of DCC and a catalytic amount of 4-pyrrolidinopyridine were added to the resulting solution, which was then stirred at room temperature for about 2 hours. Treatment and purification were then conducted in the same manner as described in Example 1, to afford 193 mg of the title compound.

Nuclear Magnetic Resonance Spectrum (270 MHz in CDCl$_3$) δ ppm: 5.83 (1H, broad triplet, J=6.8 Hz); 4.27 (1H, doublet of doublets, J=10.8 & 3.8 Hz); 1.23-1.36 (12H, broad singlet); 0.88 (3H, triplet, J=6.7 Hz).

EXAMPLE 24

Rhizoxin-13-yl 6-(undecanoylamino)hexanoate

Rhz-OOC(CH$_2$)$_5$NHCO(CH$_2$)$_9$CH$_3$ 246 mg of rhizoxin-13-yl 6-aminohexanoate and 186 mg of undecanoic acid were dissolved in toluene, and 171 mg of DCC and a catalytic amount of 4-pyrrolidinopyridine were added to the resulting solution, which was then stirred at room temperature for about 2 hours. Treatment and purification were then conducted in the same manner as described in Example 1 to afford 175 mg of the title compound.

Nuclear Magnetic Resonance Spectrum (270 MHz in CDCl$_3$) δ ppm: 5.82 (1H, broad triplet, J=6.8 Hz); 4.27 (1H, doublet of doublets, J=11.1 & 3.7 Hz); 1.20-1.36 (16H, broad singlet); 0.89 (3H, triplet, J=6.7 Hz).

EXAMPLE 25

Rhizoxin-13-yl 12-(2,2,2-trichloroethoxycarbonylamino)dodecanoate

Rhz-OOC(CH$_2$)$_{11}$NHCOOCH$_2$CCl$_3$ 2.51 g of rhizoxin and 4.69 g of 12-(2,2,2-trichloroethoxycarbouylamino)dodecanoic acid (prepared by a procedure similar to that described in Preparation 1) were dissolved in toluene, and 2.06 g of DCC, followed by a catalytic amount of 4-pyrrolidinopyridine were added to the resulting solution, which was then stirred at room temperature for about 2 hours. Treatment and purification were then conducted in the same manner as described in Example 1, to afford 2.55 g of the title compound.

Nuclear Magnetic Resonance Spectrum (270 MHz in CDCl$_3$) δ ppm: 5.01 (1H, broad singlet); 4.72 (2H, singlet); 4.26 (1H, doublet of doublets, J=10.0 & 4.1 Hz); 3.30 (2H, quartet, J=8.1 Hz); 2.38 (2H, triplet, J=8.1 Hz); 1.23-1.42 (18H, broad singlet).

EXAMPLE 26

Rhizoxin-13-yl 12-aminododecanoate

Rhz-OOC(CH$_2$)$_{11}$NH$_2$ 1.70 g of rhizoxin-13-yl 12-(2,2,2-trichloroethoxycarbonylamino)dodecanoate (prepared as described in Example 25) was dissolved in 40 ml of tetrahydrofuran, and 40 ml of a 1M aqueous solution of sodium phosphate was added to the resulting solution, followed by vigorous agitation. 60 g of zinc dust were then added to the mixture in three portions, one every hour. After three hours, treatment and purification were conducted in the same manner as described in Example 14, to afford 1.0 g of the title compound.

Nuclear Magnetic Resonance Spectrum (270 MHz in CDCl$_3$) δ ppm: 4.26 (1H, doublet of doublets, J=4.3 & 10.3 Hz); 2.88 (2H, broad triplet, J=8.1 Hz); 2.35 (2H, triplet, J=10.8 Hz); 1.66-1.78 (2H, multiplet); 1.25-1.42 (16H, multiplet).

EXAMPLE 27

Rhizoxin-13-yl 2-(propionylamino)dodecanoate

Rhz-OOC(CH$_2$)$_{11}$NHCOCH$_2$CH$_3$ 411 mg of rhizoxin-13-yl 2-aminododecanoate and 111 mg of propionic acid were dissolved in toluene, and 257 mg of DCC and a catalytic amount of 4-pyrrolidinopyridine were added to the resulting solution, followed by vigorous stirring at room temperature. Treatment and purification were then conducted in the same manner as described in Example 1, to afford 267 mg of the title compound.

Nuclear Magnetic Resonance Spectrum (270 MHz in CDCl$_3$) δ ppm: 5.43 (1H, broad singlet); 4.25 (1H, doublet of doublets, J=4.3 & 10.3 Hz); 2.18 (2H, quartet, J=7.6 Hz); 1.15 (3H, triplet, J=7.6 Hz).

EXAMPLE 28

Rhizoxin-13-yl 2-(valerylamino)dodecanoate

Rhz-OOC(CH$_2$)$_{11}$NHCO(CH$_2$)$_3$CH$_3$ 411 mg of rhizoxin-13-yl 12-aminododecanoate and 153 mg of valeric acid were dissolved in toluene, and 257 mg of DCC and a catalytic amount of 4-pyrrolidinopyridine were added to the resulting solution, which was then stirred at room temperature. Treatment and purification were then conducted in the same manner as described in Example 1, to afford 319 mg of the title compound.

Nuclear Magnetic Resonance Spectrum (270 MHz in CDCl$_3$) δ ppm: 5.40 (1H, broad singlet); 4.25 (1H, doublet of doublets, J=10.0 & 4.3 Hz); 1.24–1.42 (15H, multiplet); 0.91 (3H, triplet, J=7.0 Hz).

EXAMPLE 29

Rhizoxin-13-yl 3-(nonyloxycarbonyl)propionate

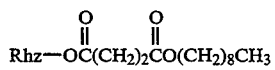

1.00 g of rhizoxin was dissolved in 160 ml of absolute toluene, and 3.2 g of succinic anhydride, 3.2 g of triethylamine and 96 mg of pyrrolidinopyridine were added to the resulting solution, which was then stirred at 60° C. for 22 hours whilst removing moisture. The reaction mixture was then washed with 150 ml each of 0.2N aqueous hydrochloric acid, with a saturated aqueous solution of sodium chloride and with a 5% w/v aqueous solution of sodium bicarbonate, in that order. The organic layer was then dried over anhydrous magnesium sulfate, and the solvent was removed by evaporation, under reduced pressure, to afford a caramel-like residue. This residue was purified by silica gel column chromatography using methylene chloride containing 5% by volume methanol as an eluent, and was then lyophilized from benzene, to afford 1.22 g of rhizoxin-13-yl 3-carboxypropionate as a yellow powder.

363 mg of the yellow powder thus formed were dissolved in 30 ml of anhydrous methylene chloride, and 216 mg of nonyl alcohol, 154 mg of DCC and 37 mg of 4-pyrrolidinopyridine were added to the resulting solution, which was then stirred at room temperature whilst removing moisture. Two hours later, insolubles were removed by filtration and the filtrate was washed with 30 ml of each 0.1N aqueous hydrochloric acid, of a saturated aqueous solution of sodium chloride and of a 5% w/v aqueous solution of sodium bicarbonate. The organic layer was then dried over anhydrous magnesium sulfate, and the solvent was removed by evaporation under reduced pressure, to afford a caramel-like residue. This residue was purified by silica gel column chromatography using a 3:2 by volume mixture of cyclohexane and ethyl acetate as eluent. Those fractions eluted first were collected and the solvent was removed by evaporation. The residue was lyophilized from benzene, to afford 214 mg of the title compound as a yellowish white powder.

Nuclear Magnetic Resonance Spectrum (270 MHz in CDCl$_3$) δ ppm: 4.27 (1H, doublet of doublets, J=10.3 & 4.0 Hz); 4.10 (2H, triplet, J=6.8 Hz); 2.60–2.75 (4H, multiplet); 1.15–1.40 (14H, broad singlet); 0.87 (3H, triplet, J=7.0 Hz).

EXAMPLE 30

Rhizoxin-13-yl 3-(undecyloxycarbonyl)]propionate

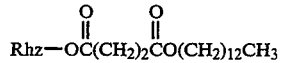

A procedure similar to that described in Example 29 was repeated, except that undecyl alcohol was used in place of nonyl alcohol, to afford 177 mg of the title compound as a yellowish white powder.

Nuclear Magnetic Resonance Spectrum (270 MHz in CDCl$_3$) δ ppm: 4.27 (1H, doublet of doublets, J=10.8 & 3.8 Hz); 4.10 (2H, triplet, J=6.8 Hz); 2.57–2.80 (4H, multiplet); 1.15–1.40 (18H, broad singlet); 0.88 (3H, triplet, J=6.8 Hz).

EXAMPLE 31

Rhizoxin-13-yl 3-( tridecyloxycarbonyl)]propionate

Rhz—OC(CH$_2$)$_2$CO(CH$_2$)$_{12}$CH$_3$

A procedure similar to that described in Example 29 was repeated, except that 258 mg of tridecyl alcohol were used in place of the nonylalcohol, to afford 212 mg of the title compound as a yellowish white powder.

Nuclear Magnetic Resonance Spectrum (270 MHz in CDCl$_3$) δ ppm: 4.27 (1H, doublet of doublets, J=10.3 & 3.2 Hz); 4.10 (2H, triplet, J=6.8 Hz); 2.60–2.80 (4H, multiplet); 1.15–1.40 (22H, broad singlet); 0.88 (3H, triplet, J=6.2 Hz).

EXAMPLE 32

Rhizoxin-13-yl 3-(benzyldithio)propionate

Rhz-OOC(CH$_2$)$_2$SSCH$_2$C$_6$H$_5$ 322 mg of benzyl 2,4-dinitrophenyl disulfide and 167 mg of silver acetate were added to a solution of 713 mg of rhizoxin-13-yl 3-mercaptopropionate in dimethylformamide, and the resulting mixture was stirred at room temperature for 2 hours. At the end of this time, the resulting precipitate was removed by filtration and the solvent was distilled off. Ethyl acetate was added to the residue and the mixture was washed with a 2% w/v aqueous solution of sodium bicarbonate and then with water. The mixture was then dried over anhydrous magnesium sulfate, after which the solvent was distilled off under reduced pressure. The residue was purified by silica gel column chromatography using a 1:1 by volume mixture of cyclohexane and ethyl acetate as eluent, to give 450 mg of the title compound.

Nuclear Magnetic Resonance Spectrum (270 MHz in CDCl$_3$) δ ppm: 7.20–7.40 (5H, multiplet); 4.25 (1H, doublet of doublets, J=3.5 & 10.0 Hz); 3.93 (2H, singlet); 2.60–2.75 (4H, broad singlet).

EXAMPLE 33

Rhizoxin-13-yl 3-methylthiopropionate

Rhz-OOC(CH$_2$)$_2$SCH$_3$ 0.45 ml of 3-methylthiopropionyl chloride, 0.25 ml of pyridine and a catalytic amount of 4-dimethylaminopyridine were added to a solution of 625 mg of rhizoxin in toluene, and the resulting mixture was stirred at room temperature for about 3 hours. At the end of this time, ethyl acetate was added to the reaction mixture and the mixture was washed in turn with 0.2N aqueous hydrochloric acid, with a saturated aqueous solution of sodium bicarbonate and with water: it was then dried over anhydrous magnesium sulfate. The solvent was then removed by distillation under reduced pressure, and the residue was purified by silica gel column chromatography, using a 1:1 by volume mixture of cyclohexane and ethyl acetate as eluent to give 450 mg of the title compound.

Nuclear Magnetic Resonance Spectrum (270 MHz in CDCl$_3$) δ ppm: 4.28 (1H, doublet of doublets, J=4.0 & 10.2 Hz); 2.65-2.85 (4H, multiplet); 2.17 (3H, singlet).

EXAMPLE 34

Rhizoxin-13-yl 3-methylthiopropionate

Rhz-OOC(CH$_2$)$_2$SCH$_3$ 1.03 g of DCC and a catalytic amount of 4-pyrrolidinopyridine were added to a solution of 1.25 g of rhizoxin and 1.20 g of 3-iodopropionic acid in toluene, and the resulting mixture was stirred at room temperature for 2 hours. At the end of this time, the reaction mixture was treated in the same manner as described in Example 1, to give 1.33 g of rhizoxin 3-iodopropionate. The whole of this ester was immediately dissolved in 20 ml of acetonitrile, and 0.92 g of the silver salt of methylmercaptan prepared at the time of use was added. The resulting mixture was stirred at room temperature for 8 hours, after which the precipitate was filtered off. The solvent was then removed by distillation under reduced pressure, and ethyl acetate was added to the residue. The resulting mixture was washed with a 5% w/v aqueous solution of sodium bicarbonate and with a saturated aqueous solution of sodium chloride, in that order, after which it was dried over anhydrous sodium sulfate. The solvent was then removed by distillation under reduced pressure, and the residue was purified by silica gel column chromatography, using a 1:1 by volume mixture of cyclohexane and ethyl acetate as eluent, to give 970 mg of the title product.

PREPARATION 1

3-(2,2,2-Trichloroethoxycarbonylamino)propionic acid 15.06 g of β-alanine were dissolved in 170 ml of 1N aqueous sodium hydroxide, and 7.5 g of 2,2,2-trichloroethoxycarbonyl chloride and 340 ml of 1N aqueous sodium hydroxide were then added dropwise over 5 hours to the resulting solution, whilst ice-cooling. After completion of the dropwise addition, the temperature of the mixture was allowed to return to room temperature, and then the mixture was stirred overnight. At the end of this time, 300 ml of water and 200 ml of diethyl ether were added to the mixture and insolubles were dissolved, after which the organic layer was separated off. The aqueous layer was washed twice with 300 ml of ethyl acetate, and it was then adjusted to a pH value of 1.5 by the addition of concentrated aqueous hydrochloric acid, whilst ice-cooling. It was then extracted with 300 ml of ethyl acetate. The extract was washed with a saturated aqueous solution of sodium chloride and dried over anhydrous magnesium sulfate, after which the solvent was evaporated off.

100 ml each of cyclohexane and ethyl acetate were added to the residue, and the resulting mixture was left to stand overnight at room temperature. The resulting precipitate was collected by filtration, washed with 50 ml of cyclohexane and dried, to afford 33.8 g of the title compound, melting at 89.4° to 91.0° C.

6-(2,2,2-Trichloroethoxycarbonylamino)hexanoic acid (melting at 87.3° to 89.0° C.) and 12-(2,2,2,-trichloroethoxycarbonylamino)dodecanoic acid (melting at 69.8° to 72.6° C.) were also synthesized using the same procedures.

PREPARATION 2

12-Trichloroethoxycarbonyloxydodecanoic acid 4.32 g of 12-hydroxydodecanoic acid were dissolved in 200 ml of ethyl acetate and 30 ml of water, and 5.5 g of diphenyldiazomethane were added to the resulting solution, which was then stirred at room temperature overnight. At the end of this time, about 10 ml of acetic acid was added to the resulting mixture to decompose the excess diphenyldiazomethane, after which the mixture was washed with 100 ml of water and the organic layer was separated. The organic layer was then washed twice, each time with 100 ml of a 5% w/v aqueous solution of sodium bicarbonate and with a saturated aqueous solution of sodium chloride. The washed organic layer was then dried over anhydrous magnesium sulfate and the solvent was removed by evaporation under reduced pressure, to afford 9.2 g of a thickly viscous yellow oily residue. This residue was purified by silica gel column chromatography using cyclohexane containing 10% by volume ethyl acetate as eluent, to afford 5.2 g of benzhydryl 12-hydroxydodecanoate as a thickly viscous pale yellow oily substance.

The whole of this benzhydryl 12-hydroxydodecanoate was dissolved in 400 ml of anhydrous ethyl acetate, and 13.7 ml of pyridine were added to the resulting solution, whilst ice-cooling, after which 3.48 g of trichloroethoxycarbonyl chloride dissolved in 10 ml of ethyl acetate were added dropwise over about 15 minutes. Insoluble salts were precipitated, after which the temperature of the mixture was allowed to return to room temperature, and the mixture was then stirred for a further 2 hours. The reaction mixture was then washed with 200 ml of 0.5N aqueous hydrochloric acid, after which it was washed with 100 ml each of a saturated aqueous solution of sodium chloride and of a 5% w/v aqueous solution of sodium bicarbonate. The organic layer was then dried over anhydrous magnesium sulfate, after which the solvent was removed by evaporation under reduced pressure. The residue thus obtained was purified by silica gel column chromatography using cyclohexane containing 20% by volume ethyl acetate as eluent, to afford a colorless and transparent viscous oil. The whole of this oil was dissolved in 5 ml of anisole, and 20 ml of trifluoroacetic acid was added to the resulting solution, whilst ice-cooling. The mixture was then left to stand for 1 hour. At the end of this time, the solvent was removed by evaporation under reduced pressure. This evaporating operation was repeated three times by adding 30 ml of toluene and dissolving the residue in 100 ml of a mixture of ethyl acetate and water. After this, 100 ml of a saturated aqueous solution of sodium bicarbonate was added to the organic layer, which emulsified the resulting mixture, and then the pH of the mixture was adjusted to a value of about 1 by the addition of concentrated hydrochloric acid. After the organic layer had been separated, it was washed with 100 ml of a saturated aqueous solution of sodium chloride and dried over anhydrous magnesium sulfate. The solvent was then removed by evaporation under reduced pressure, to afford an oily residue. The residue was purified by silica gel column chromatography using a 2:1 by volume mixture of cyclohexane and ethyl acetate as eluent and then recrystallized from hexane to afford 3.96 g of the title compound as white plate-like crystals, melting at 44.6° to 46.4° C.

BIOLOGICAL ACTIVITY

The test animals employed were female mice, 8 weeks of age, of the $CDF_1$ strain, each weighing 21–25 g. The mice were divided into groups, each of 6 mice, and all mice within the group were treated identically. Into each mouse was implanted intraperitoneally $1 \times 10^6$ cells of the mouse leukemia p-388.

The test compounds shown in the following Table were dissolved in a small amount of dimethylacetamide. and immediately thereafter physiological saline containing 1% w/v. Tween 80 (registered trade mark) was added to the solution to form a suspension. The suspension was administered intraperitoneally on the first, fifth and ninth days following implantation of the leukemia cells. The period for which the mice survived was determined. A control group was treated identically, except that no active compound was administered.

The anti-tumor effect is shown in the following Table as the increase in life span [ILS (%)], calculated from the following equation [R. I. Geran etal, Cancer Chemother. Rept., 3 (1972)]:

$$ILS (\%) = (Dt/Dc - 1) \times 100$$

where

Dt=average number of days survival by the test group; and

Dc=average number of days survival by the control group.

In this test, Dc was 9–10 days.

The compounds of the invention are identified in the following Table by the numbers assigned to them in the foregoing list. Compounds A and B are rhizoxin and rhizoxin-13-yl hexadecanoate (Compound No. 62 of U.S. Pat. No. 4,791,128), respectively.

TABLE

| Cpd No. | dose (mg/kg) | ILS (%) | evaluation | 60 days survival |
|---|---|---|---|---|
| 3 | 32 | 84 | + | 0/6 |
| 27 | 8 | 217 | +++ | 2/5 |
| 28 | 16 | 129 | ++ | 1/6 |
| 31 | 8 | 470 | +++ | 4/6 |
| 32 | 8 | 222 | +++ | 0/6 |
| 33 | 32 | 89 | + | 0/6 |
| 47 | 4 | 119 | ++ | 0/6 |
| 49 | 4 | 559 | +++ | 4/5 |
| 50 | 16 | 267 | +++ | 0/6 |
| 51 | 4 | 243 | +++ | 1/6 |
| 56 | 4 | 139 | ++ | 0/5 |
| 57 | 8 | 206 | +++ | 0/6 |
| 58 | 4 | 131 | ++ | 1/6 |
| 78 | 16 | 135 | ++ | 0/6 |
| 83 | 32 | 174 | ++ | 0/5 |
| 84 | 16 | 123 | ++ | 0/6 |
| 85 | 16 | 144 | ++ | 0/6 |
| 91 | 32 | 177 | ++ | 0/6 |
| 92 | 16 | 125 | ++ | 0/6 |
| 93 | 16 | 153 | ++ | 1/6 |
| 98 | 16 | 542 | +++ | 3/6 |
| 102 | 8 | 253 | +++ | 1/6 |
| 105 | 16 | 190 | ++ | 1/6 |
| 106 | 8 | 145 | ++ | 0/6 |
| 107 | 8 | 223 | +++ | 0/6 |
| 111 | 8 | 403 | +++ | 0/5 |
| 114 | 16 | 180 | ++ | 1/6 |

TABLE-continued

| Cpd No. | dose (mg/kg) | ILS (%) | evaluation | 60 days survival |
|---|---|---|---|---|
| 115 | 8 | 307 | +++ | 3/6 |
| 116 | 8 | 471 | +++ | 5/6 |
| A | 2 | 85 | + | 0/6 |
| B | 12 | 162 | ++ | 0/6 |

It can be seen from the results in the above Table that all of the compounds tested are more effective than rhizoxin itself and that the majority are substantially more effective than the prior compound, rhizoxin-13-yl hexadecanoate, which is regarded as the best of the compounds disclosed in U.S. Pat. No. 4,791,128.

We claim:

1. A compound of formula (I):

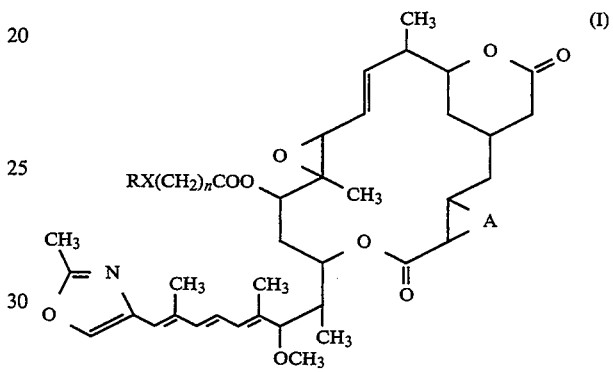

in which n represents an integer of from 2 to 11,

A represents an oxygen atom,

X represents a sulfur atom or an NH group and when X represents a sulfur atom, R represents a $C_{1-4}$alkylthio group, a benzylthio group and a Rhz-OOC(CH$_2$)$_2$S group;

Rhz represents a group of formula (II):

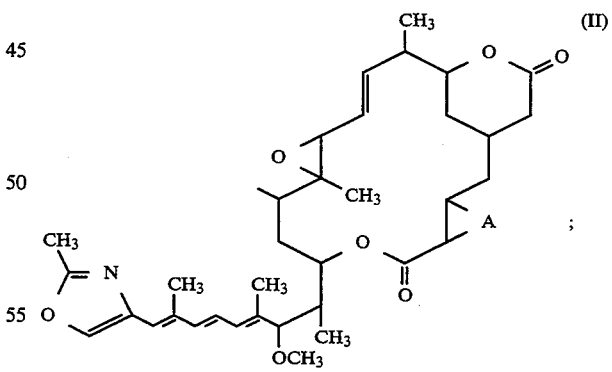

when X represents an NH group, R represents a hydrogen atom.

2. The compound of claim 1, selected from the group consisting of rhizoxin-13-yl 3-methylthiopropionate and pharmaceutically acceptable salts and esters thereof.

3. A pharmaceutical composition comprising an effective anti-tumor amount of an anti-tumor agent in admixture with a pharmaceutically acceptable carrier or diluent, wherein the anti-tumor agent is at least one compound selected from the group consisting of compounds of formula (I) and pharmaceutically acceptable salts and esters thereof ring-opened.

4. The composition of claim 3, wherein said anti-tumor agent is selected from the group consisting of rhizoxin-13-yl 3-methylthiopropionate and pharmaceutically acceptable salts and esters thereof.

5. A method of treating an animal suffering from tumors, by administering thereto an effective amount of an anti-tumor agent, wherein said anti-tumor agent is at least one compound selected from the group consisting of compounds of formula (I) and pharmaceutically acceptable salts and esters thereof.

6. The method of claim 5, wherein said anti-tumor agent is selected from the group consisting of rhizoxin-13-yl 3-methylthiopropionate and pharmaceutically acceptable salts and esters thereof.

* * * * *

UNITED STATES PATENT AND TRADEMARK OFFICE
CERTIFICATE OF CORRECTION

PATENT NO. : 5,391,564
DATED : February 21, 1995
INVENTOR(S) : KANEKO et al It is certified that error appears in the above-identified patent and that said Letters Patent is hereby corrected as shown below:

Title Page: [57], Abstract, 3rd line from the end, after "dialkylphosphono" insert --,--.

Title Page: [56], under "References Cited" insert

--U.S. PATENT DOCUMENTS

| | | | |
|---|---|---|---|
| 4,680,178 | 7/1987 | Kiyoto et al | 514/374 |
| 4,791,128 | 12/1988 | Okuda et al | 548/235 |

FOREIGN PATENT DOCUMENTS

| | | |
|---|---|---|
| 246 380 | 10/1988 | Japan |
| 931 186 | 5/1986 | Japan |
| 0 145 177 | 6/1985 | Europe |

OTHER PUBLICATIONS

CHEMICAL ABSTRACTS, Vol. 103, 1985, page 374

THE MERCK INDEX, An Encyclopedia of Chemicals, Drugs and Biologicals, 10th Edition, 1983, page 1408.

Iwasaki et al, THE JOURNAL OF ANTIBIOTICS, "STUDIES ON MACROCYCLIC LACTONE ANTIBIOTICS VII, Structure of a Phytotoxin 'RHIZOXIN' produced by Rhizopus Chinensis", April 1984, pages 354-362

Chem. Abstracts, Vol. 110, 2124965 (1989). --

UNITED STATES PATENT AND TRADEMARK OFFICE
CERTIFICATE OF CORRECTION

PATENT NO. : 5,391,564

DATED : February 21, 1995

INVENTOR(S) : KANEKO et al

It is certified that error appears in the above-identified patent and that said Letters Patent is hereby corrected as shown below:

Column 1, line 17, delete "ting" and insert --ring--.

Column 45, line 2, Claim 3, delete "ring-opened".

Signed and Sealed this

Twenty-third Day of April, 1996

Attest:

BRUCE LEHMAN

Attesting Officer

Commissioner of Patents and Trademarks